United States Patent
Meyers

(10) Patent No.: US 6,569,667 B1
(45) Date of Patent: May 27, 2003

(54) 26335, A NOVEL HUMAN SERINE/THREONINE DEHYDRATASE AND USES THEREOF

(75) Inventor: Rachel Meyers, Newton, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 09/843,297

(22) Filed: Apr. 25, 2001

Related U.S. Application Data

(60) Provisional application No. 60/199,801, filed on Apr. 26, 2000.

(51) Int. Cl.$^7$ .......................... C12N 9/88; C12N 15/60; C12Q 1/68

(52) U.S. Cl. ..................... 435/232; 435/6; 435/320.1; 435/252.3; 536/23.2

(58) Field of Search ................. 435/232, 6, 252.3, 435/975, 320.1; 536/23.2

(56) References Cited

U.S. PATENT DOCUMENTS 6,277,619 B1 * 8/2001 Lai et al. .................... 435/232

FOREIGN PATENT DOCUMENTS

| WO | WO 99/06554 A2 | 2/1999 |
|---|---|---|
| WO | WO 01/53312 A1 | 7/2001 |

OTHER PUBLICATIONS

EBI Acc. No. J05037, Ogawa, H. et al., "Human serine dehydratase mRNA, complete cds" (Apr. 23, 1990).
EBI Acc. No. P20132, Ogawa, H. et al., "L–serine dehydratase (EC 4.2.1.13)(L–Serine Deaminase)" (Feb. 1, 1991).
EMBL Acc. No. BC009849, Strausberg, R., "Homo sapiens, clone MGC:15400 Image:4040570, mRNA, complete cds" (Jul. 7, 2001).
Leoncini, R. et al. "Restoration of rat liver L–threonine dehydratase activity by pyrdoxamine 5'–phosphate: the half–transaminating activity of L–threonine dehydratase and its regulatory role" Biochemica et Biophysica Acta 1425(2):411–418 (Oct. 23, 1998).
Alexander FW, et al. Evolutionary relationships among pyridoxal–5'–phosphate–dependent enzymes. Regio–specific alpha, beta and gamma families. Eur J Biochem. Feb. 1, 1994; 219(3):953–60.
Braunstein AE, et al. The beta–replacement–specific pyridoxal–P–dependent lyases. Adv Enzymol Relat Areas Mol Biol. 1984;56:1–89.
Burgisser DM, et al. Expression and characterization of recombinant human and rat liver 6–pyruvoyl tetrahydropterin synthase. Modified cysteine residues inhibit the enzyme activity. Eur J Biochem. Jan. 15, 1994;219(1–2):497–502.

Datta P, et al. Covalent structure of biodegradative threonine dehydratase of *Escherichia coli*: homology with other dehydratases. Proc Natl Acad Sci U S A. Jan. 1987;84(2):393–7.
Fowler B. Recent advances in the mechanism of pyridoxine–responsive disorders. J. Inherit Metab Dis. 1985;8 Suppl 1:76–83.
Results of BLASTN search of GenBank EST database (dBest) using 26335 nucleotide sequence (2000).
Results of BLASTN search of Nucleic Acid Patent database using 26335 nucleotide sequence (2000).
Results of BLASTN search of Nucleic Acid Patent database using 26335 nucleotide sequence (2000).
Results of BLASTN search of GenBank Nucleotide database using 26335 nucleotide sequence (2000).
GenBank Accession No. Y00752 Rat mRNA for serine dehydratase (EC 4.3.1.13) (1997).
GenGank Accession No. J03863 Rat serine dehydratase (SDH2) mRNA, complete cds. (1993).
GenBank Accession No. AI953998 wx78c12.x1 NCI_CGAP_Ov38 Homo sapiens cDNA clone Image: 254782 3'similar to SW:SDHL_RAT p09367 L–Serine Dehydratase;, mRNA sequence (2000).
GenBank Accession No. AI741818 wg29c09.x1 Soares_NSF_F8_9W_OT_PA_P_S1 Homo sapiens cDNA clone Image: 2366512 3'similar to SW:SDHL_RAT P09367 L–Serine Dehydrates;, mRNA sequence (1999).
Grabowski R, et al. Bacterial L–serine dehydratases: a new family of enzymes containing iron–sulfur clusters. Trends Biochem Sci. 1993 Aug.; 18(8):297–300.
Hofmeister AE, et al. L–serine and L–threonine dehydratase from Clostridium propionicum., Two enzymes with different prosthetic groups. Eur J Biochem. Jul. 15, 1993;215(2):341–9.
Kraus JP. Biochemistry and molecular genetics of cystathionine beta–synthase deficiency. Eur J Pediatr. Apr. 1998; 157 Suppl 2:S50–3.
Marceau M, et al. D–serine dehydratase from *Escherichia coli*. DNA sequence and identification of catalytically inactive glycine to aspartic acid variants. J Biol Chem. Nov. 15, 1988; 263(32):16926–33.

(List continued on next page.)

Primary Examiner—Charles L. Patterson, Jr.
(74) Attorney, Agent, or Firm—Lahive & Cockfield LLP; Amy E. Mandragouras; Maria Laccotripe Zacharakis

(57) ABSTRACT

The invention provides isolated nucleic acid molecules, designated DHY nucleic acid molecules, which encode novel DHY-related dehydratase molecules. The invention also provides antisense nucleic acid molecules, recombinant expression vectors containing DHY nucleic acid molecules, host cells into which the expression vectors have been introduced, and nonhuman transgenic animals in which a DHY gene has been introduced or disrupted. The invention still further provides isolated DHY proteins, fusion proteins, antigenic peptides and anti-DHY antibodies. Diagnostic methods utilizing compositions of the invention are also provided.

26 Claims, 7 Drawing Sheets

OTHER PUBLICATIONS

Noda C, et al. Primary structure of rat liver serine dehydratase deduced from the cDNA sequence. FEBS Lett. Jul. 18, 1988; 234(2):331–5.

Ogawa H, et al. Human liver serine dehydratase. cDNA cloning and sequence homology with hydroxyamino acid dehydratases from other sources. J Biol Chem. Sep. 25, 1989; 264(27):15818–23.

Ogawa H, et al. Rat serine dehydratase gene codes for two species of mRNA of which only one is translated into serine dehydratase. J Biol Chem. Aug. 25, 1990;265(24):14407–13.

Ogawa H, et al. Isolation and nucleotide sequence of the cDNA for rat liver serine dehydratase mRNA and structures of the 5'and 3'flanking regions of the serine dehyrdratase gene. Proc Natl Acad Sci U S A. Aug. 1988;85(16):5809–13.

Parsot C. Evolution of biosynthetic pathways: a common ancestor for threonine synthase, threonine dehydratase and D–serine dehydratase. EMBO J. Nov. 1986;5(11):3013–9.

Schiltz E, et al. Sequence of *Escherichia coli* D–serine dehydratase. Location of the pyridoxal–phosphate binding site. FEBS Lett. Nov. 2, 1981;134(1):57–62.

* cited by examiner

```
Input file Fbh26335FL.seq; Output File 26335.trans
Sequence length 1327

CACGCGTCCGGGAAAGAGCTGGTTCCCTGGCAGGCTGGAGGGCAGGAGCTGGGGCCACGCTGGTCTGGGATAGTTGGGC

M   D   G   P   V   A   E   H   A   K   Q   E   P    13
AGGGAGGCTGTCTACCTGGTCTCCAGA     ATG GAC GGC CCT GTG GCA GAG CAT GCC AAG CAG GAG CCC  39

F   H   V   V   T   P   L   L   E   S   W   A   L   S   Q   V   A   G   M   P       33
TTT CAC GTG GTC ACA CCT CTG TTG GAG AGC TGG GCG CTG TCC CAG GTG GCG GGC ATG CCT      99

V   F   L   K   C   E   N   V   Q   P   S   G   S   F   K   I   R   G   I   G       53
GTC TTC CTC AAG TGT GAG AAT GTG CAG CCC AGC GGC TCC TTC AAG ATT CGG GGC ATT GGG     159

H   F   C   Q   E   M   A   K   K   G   C   R   H   L   V   C   S   S   G   G       73
CAT TTC TGC CAG GAG ATG GCC AAG AAG GGA TGC AGA CAC CTG GTG TGC TCC TCA GGG GGT     219

N   A   G   I   A   A   A   Y   A   A   R   K   L   G   I   P   A   T   I   V       93
AAT GCG GGC ATC GCT GCT GCC TAT GCT GCT AGG AAG CTG GGC ATT CCT GCC ACC ATC GTG     279

L   P   E   S   T   S   L   Q   V   V   Q   R   L   Q   A   E   G   A   E   V      113
CTC CCC GAG AGC ACC TCC CTG CAG GTG GTG CAG AGG CTG CAG GCG GAG GGG GCC GAG GTT     339

Q   L   T   G   K   V   W   D   E   A   N   L   R   A   Q   E   L   A   K   R      133
CAG CTG ACT GGA AAG GTC TGG GAC GAG GCC AAT CTG AGG GCG CAA GAG TTG GCC AAG AGG     399

D   G   W   E   N   V   P   P   F   D   H   P   L   I   W   K   G   H   A   S      153
GAC GGC TGG GAG AAT GTC CCC CCG TTT GAC CAC CCC CTA ATA TGG AAA GGC CAC GCC AGC     459

L   V   Q   E   L   K   A   V   L   R   T   P   P   G   A   L   V   L   A   V      173
CTG GTG CAG GAG CTG AAA GCA GTG CTG AGG ACC CCA CCA GGT GCC CTG GTG CTG GCA GTT     519

G   G   G   G   L   L   A   G   V   V   A   G   L   L   E   V   G   W   Q   H      193
GGG GGT GGG GGT CTC CTG GCC GGG GTG GTG GCT GGC CTG CTG GAG GTG GGC TGG CAG CAT     579

V   P   I   I   A   M   E   T   H   G   A   H   C   F   N   A   A   I   T   A      213
GTA CCC ATC ATT GCC ATG GAG ACC CAT GGG GCA CAC TGC TTC AAT GCG GCC ATC ACA GCC     639

G   K   L   V   T   L   P   D   I   T   S   V   A   K   S   L   G   A   K   T      233
GGC AAG CTG GTC ACA CTT CCA GAC ATC ACC AGT GTG GCC AAG AGC CTG GGT GCC AAG ACG     699

V   A   A   R   A   L   E   C   M   Q   V   C   K   I   H   S   E   V   V   E      253
GTG GCC GCT CGG GCC CTG GAG TGC ATG CAG GTG TGC AAG ATT CAC TCT GAA GTG GTG GAG     759

D   T   E   A   V   S   A   V   Q   Q   L   L   D   D   E   R   M   L   V   E      273
GAC ACC GAG GCT GTG AGC GCT GTG CAG CAG CTC CTG GAT GAT GAG CGT ATG CTG GTG GAG     819

P   A   C   G   A   A   L   A   A   I   Y   S   G   L   L   R   R   L   Q   A      293
CCT GCC TGT GGG GCA GCC TTA GCA GCC ATC TAC TCA GGC CTC CTG CGG AGG CTC CAG GCC     879

E   G   C   L   P   P   S   L   T   S   V   V   V   I   V   C   G   G   N   N      313
GAG GGC TGC CTG CCC CCT TCC CTG ACT TCA GTT GTG GTA ATC GTG TGT GGA GGC AAC AAC     939

I   N   S   R   E   L   Q   A   L   K   T   H   L   G   Q   V   *                  330
ATC AAC AGC CGA GAG CTG CAG GCC TTG AAA ACC CAC CTG GGC CAG GTC TGA                 990
```

Fig. 1A

GGGGTCCCATCCTGGCCCCAAAGACCCCTGAGAGGCCCATGGACAGTCCTGTGTCTGGATGAGGAGGACTCAGTGCTGG
CAGATGGCAGTGGAAGCTGCCCTGTGCAACTGTGCTGGCTGCCTCCTGAAGGAAGCCCTCCTGGACTGCTTCTTTTGGC
TCTCCGACAACTCCGGCCAATAAACACTTTCTGAATTGAGTTTGCGAATAAAAAAAAAAAAAAAAAAAAAAAAA

Fig. 1B

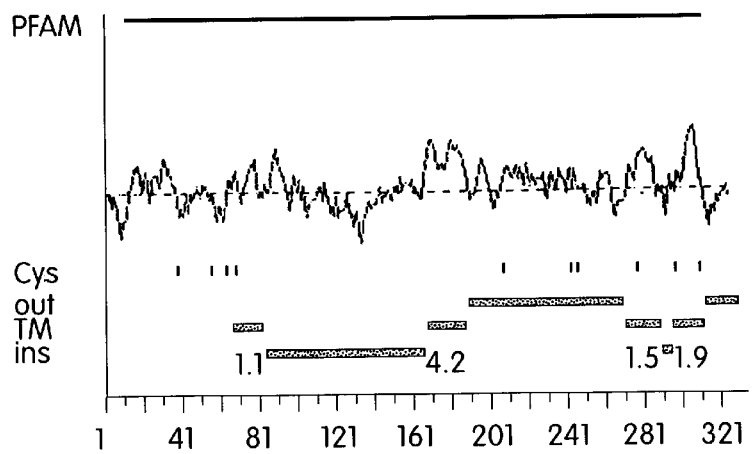

>26335
MDGPVAEHAKQEPFHVVTPLLESWALSQVAGMPVFLKCENVQPSGSFKIRGIGHFCQEMA
KKGCRHLVCSSGGNAGIAAAYAARKLGIPATIVLPESTSLQVVQRLQAEGAEVQLTGKVW
DEANLRAQELAKRDGWENVPPFDHPLIWKGHASLVQELKAVLRTPPGALVLAVGGGGLLA
GVVAGLLEVGWQHVPIIAMETHGAHCFNAAITAGKLVTLPDITSVAKSLGAKTVAARALE
CMQVCKIHSEVVEDTEAVSAVQQLLDDERMLVEPACGAALAAIYSGLLRRLQAEGCLPPS
LTSVVVIVCGGNNINSRELQALKTHLGQV

Fig. 2

Transmembrane Segments Predicted by MEMSAT

| Start | End | Orient | Score |
|---|---|---|---|
| 67 | 83 | out-->ins | 1.1 |
| 167 | 187 | ins-->out | 4.2 |
| 270 | 288 | out-->ins | 1.5 |
| 295 | 311 | ins-->out | 1.9 |

>26335
MDGPVAEHAKQEPFHVVTPLLESWALSQVAGMPVFLKCENVQPSGSFKIRGIGHFCQEMA
KKGCRHLVCSSGGNAGIAAAYAARKLGIPATIVLPESTSLQVVQRLQAEGAEVQLTGKVW
DEANLRAQELAKRDGWENVPPFDHPLIWKGHASLVQELKAVLRTPPGALVLAVGGGGLLA
GVVAGLLEVGWQHVPIIAMETHGAHCFNAAITAGKLVTLPDITSVAKSLGAKTVAARALE
CMQVCKIHSEVVEDTEAVSAVQQLLDDERMLVEPACGAALAAIYSGLLRRLQAEGCLPPS
LTSVVVIVCGGNNINSRELQALKTHLGQV

Fig. 3

Prosite Pattern Matches for 26335

Prosite version: Release 12.2 of Fenruary 1995

>PS00005|PDOC00005|PKC_PHOSPHO_SITE Protein kinase C phosphorylation site.

Query: 46      SFK      48
Query: 116     TGK      118

>PS00006|PDOC00006|CK2_PHOSPHO_SITE Casein kinase II phosphorylation site.

Query: 218     TLPD     221

>PS00008|PDOC00008|MYRISTYL N-myristoylation site.

Query: 72      GGNAGI   77
Query: 87      GIPATI   92
Query: 176     GGLLAG   181
Query: 277     GAALAA   282
Query: 311     GNNINS   316

>PS00165|PDOC00149|DEHYDRATASE_SER_THR Serine/threonine dehydratases
                  pyridoxal-phosphate attachment site
Query: 39      ENVQPSGSFKIRGI   52

Fig. 4

Protein Family / Domain Matches, HMMer Version 2
Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - - - - - - - - - -
HMM FILE:                  /prod/ddm/seqanal/PFAM/pfam5.2/Pfam
Sequence file:             /prod/ddm/wspace/orfanal/oa-script.260.seq
- - - - - - - - - - - - - - - - - - - - - - - - - - - - - - - - - - - -
Query: 26335

Scores for sequence family classification (score includes all domains):
Model            Description                              Score    E-value   N
--------         -----------                              -----    -------  ---
S_T_dehydratese  Pyridoxal-phosphate dependent enzyme     229.5    4.8e-65   1

Parsed for domains:
Model            Domain   seq-f  seq-t     hmm-f  hmm-t      score    E-value
--------         ------   -----  -----     -----  -----      -----    -------
S_T_dehydratase  1/1      11     311   ..  1      378   []   229.5    4.8e-65

Alignments of top-scoring domains:
S_T_dehydratase: domain 1 of 1, from 11 to 311: score 229.5, E = 4.8e-65
                *->vtelignTPLvrlnrlskelgeglganaaveiylKlEdlnGPtGSfK
                   + +    TPL ++  ls       g++    ++lK+E  + P+GSfK
    26335    11  QEPFHVVTPLLESWALS----QVAGMP----VFLKCENVQ-PSGSFK  48

DRglalnmillAeklgkkggivpgtvqveskttiiEptsGNtGialAlaa
                +Rg + + +   k g++++++ +                GN+Gia+A+aa
    26335    49  IRG-IGHFCQEMAKKGCRHLVCSS-------------GGNAGIAAAYAA  83 allGlkctivMPatdtsreKraqlralGAelvvvpvagGgsddladaiak
                ++lG+++tiv P+  ts++  +++l a+GA   +v ++g   +d+a+  a+
    26335    84  RKLGIPATIVLPES-TSLQVVQRLQAEGA---EVQLTG-KVWDEANLRAQ 128

AeelaeenpenayllnqaaGpfdnPanpeiagqktigpEIweQlggkeis
                ela++++   +  +++      fd+P +++  g+  ++++E+++ l+  +
    26335   129  --ELAKRDG--WENVPP----FDHPLIWK--GHASLVQELKAVLRTP--- 165 lgrlpDavvapvGgGGtitGiarylKelnpdgkIdvlelpvkvigVEPeg
                   p a+v+  vGgGG+++G+  ++l  e     ++        +v +i+  E+  g
    26335   166  ----PGALVLAVGGGGLLAGVVAGLLEVGWQ--------HVPIIAMETHG 203 savlsgslkatltlagkpGplhgrdskyllQDepvtlpetksigiGlgvp
                ++++++++                  +G+                vtlp+++s  +   lg +
    26335   204  AHCFNAAIT--------AGK------------LVTLPDITSVAKSLGAK 232 rvgefvppildelldrrqgidevvtvtdeealeaarlLareEGilvgpss
                +v++++  +  ++                 ++v+d+ea+  a  ++L  ++E++lv+p++
    26335   233  TVAARALECMQVCKI------HSEVVEDTEAVSAVQQLLDDERMLVEPAC 276 gaavaaalklakegkkplnkgk.......tiVvilsgg<-*
                gaa+aa  ++    +    l  +++   +++ + +Vvi++gg
    26335   277  GAALAAIYSGLLR---RLQAEGclppsltSVVVIVCGG     311

Fig. 5

ProDom Matches

>206 p99.2 (175) TRPB(29) CYSK(16) THRC(15)  // LYASE SYNTHASE PYRIDOXAL
    PHOSPHATE BIOSYNTHESIS TRYPTOPHAN CYSTEINE THREONINE BETA CHAIN
    Length = 374

Score = 88 (36.0 bits), Expect = 0.00014, Sum P(2) = 0.00014
 Identities = 36/113 (31%), Positives = 52/113 (46%)

Query:    18 TPLLESWALSQVAGMP--VFLKCENVQ-P--SGSFKIRGIGHFCQE-----MAKKGCRHL 67
             TPL+    LS+  G    ++LK E +  P   SGS+K RG     E     + K G + +
Sbjct:    17 TPLVRLNNLSERLGCKAAIYLKKEELMNPTGSGSYKDRGAYSMISEAEEEGLIKPGKKSV 76

Query:    68 VCSSXXXXXXXXXXX--XRKLGIPATIVLPESTSLQV--VQRLQAEGAEVQLT 116
              + S              +LG+   IV+PES S +    V  L+A GAE+ LT
Sbjct:    77 IVESTSGNTGAVALAMVAARLGLKCVIVMPESMSQEQKRVSMLRAYGAEIVLT 129

Score = 69 (29.3 bits), Expect = 0.00014, Sum P(2) = 0.00014
 Identities = 26/91 (28%), Positives = 42/91 (46%)

Query:   196 IIAMETHGAHCFNAAITAGKLVT--LPDITSVAKSLGAKTVAARALECMQVCKIHSEVVE 253
             +  +E  GA   + A+ +GK++     +  +VA          E +QV    +E V
Sbjct:   249 LAGVEAGGAGSLHGALKSGKMQPHKIQGVGTVAVPANLDYPGEVVDEVIQVSSDRAEAVS 308

Query:   254 --DTEAVSAVQQLLDDERMLVEPACGAALAA 282
               D EA+ A   L + E ++ EPA  AA+AA
Sbjct:   309 VSDEEALEAGLLLGESEGIVPEPASAAAIAA 339

26335, A NOVEL HUMAN SERINE/THREONINE DEHYDRATASE AND USES THEREOF

RELATED APPLICATIONS

This application claims priority to U.S. Provisional Patent Application No. 60/199,801, filed on Apr. 26, 2000, incorporated herein in its entirety by reference.

BACKGROUND OF THE INVENTION

The biosynthesis and metabolism of amino acids is of critical importance in many metabolic and catabolic pathways in cells, and is fundamental to the production of cellular proteins. A wide array of enzymes facilitate the synthesis, interconversion, and degradation of amino acids, including transaminases, oxidases, reductases, dehydrogenases, and kinases, among many others. One such family of enzymes, the serine and threonine dehydratases, catalyze the irreversible deamination of serine or threonine to pyruvate or 2-oxobutyrate, respectively.

The reaction mechanism for these enzymes has been characterized (Snell and Di Mari (1970) The Enzymes (Boyer, P. D., ed.), Academic Press: $3^{rd}$ ed. Vol. 2: 335–370; and Ogawa et al. (1989) Biochim. Biophys. Acta 996: 139–141). First, a Schiff base is formed between a pyridoxal-5'phosphate cofactor and a specific lysine residue which is strictly conserved within the serine and threonine dehydratase family. A new Schiff base is subsequently formed between the cofactor and the hydroxyamino acid by transimination, catalyzing the removal of the α-proton through stabilization of the resulting carbanion by the planar π-system of the prosthetic group. The hydroxyl group is eliminated, and the resultant enamine is freed by a second transimination. A tautomerization step results in the formation of a ketimine, which hydrolyses to the 2-oxoacid and ammonia (Gabowski et al. (1993) Trends in Biological Sciences 18: 297–300). A subclass of the serine dehydratases found in anaerobic bacteria substitutes an iron-sulfur cofactor for pyridoxal-5'-phosphate, and exhibits an altered reaction mechanism with similarities to the mechanism of aconitase (Hofmeister et al. (1993) Eur J Biochem 215(2):341–9). Threonine dehydratases, in general, are able to deaminate either threonine or serine, while the serine dehydratases have been found to be specific for the deamination of serine (Grabowski et al. (1992) Eur. J. Biochem. 199:89–94; and Alfoldi et al. (1968) J. Bacteriol. 96:1512–1518).

Members of the serine and threonine dehydratase family are found in nearly all organisms, from bacteria to yeast to mammals. Alignments of the amino acid sequences of family members from disparate organisms have revealed two conserved regions, termed C1 and C2. The conserved C1 domain is located approximately 50 amino acid residues from the N-terminus of the enzyme, and includes the consensus sequence (G)S(F)K(I)RG (Datta et al. (1987) Proc. Natl. Acad. Sci. USA 84: 393–397). This region of the protein has been shown to bind the cofactor, pyridoxal-5'-phosphate, at the conserved lysine residue (Schlitz and Schmitt (1981) FEBS Lett. 134:57–62). Conserved region C2 is located in the central region of the amino acid sequences of these enzymes, and is predicted to have a beta sheet-coil-beta sheet structure (Datta et al., supra). C2 is rich in glycine, and is thought to be involved in the catalytic activity of the enzymes (Marceau et al. (1988) J. Biol. Chem. 263: 16926–16933).

Serine and threonine dehydratases play key roles in the degradation of threonine and serine, as well as in the biosynthesis of isoleucine and the production of pyruvate and 2-oxobutyrate, both of which serve as substrates for energy metabolism or biosynthetic purposes. As such, the activity of these dehydratases contributes to the ability of the cell to grow and differentiate, to proliferate, and to communicate and interact with other cells (for example, through the production of growth factors and cytokines).

SUMMARY OF THE INVENTION

The present invention is based, at least in part, on the discovery of novel members of the family of dehydratase molecules, referred to herein as DHY nucleic acid and protein molecules. The DHY nucleic acid and protein molecules of the present invention are useful as modulating agents in regulating a variety of cellular processes, e.g., cellular proliferation, growth, differentiation, or migration. Accordingly, in one aspect, this invention provides isolated nucleic acid molecules encoding DHY proteins or biologically active portions thereof, as well as nucleic acid fragments suitable as primers or hybridization probes for the detection of DHY-encoding nucleic acids.

In one embodiment, a DHY nucleic acid molecule of the invention is at least 50%, 55%, 60%, 65%, 70%, 75%, 80%, 85%, 90%, 95%, 96%, 97%, 98%, 99% or more identical to the nucleotide sequence (e.g., to the entire length of the nucleotide sequence) shown in SEQ ID NO:1 or 3, or a complement thereof.

In a preferred embodiment, the isolated nucleic acid molecule includes the nucleotide sequence shown in SEQ ID NO:1 or 3, or a complement thereof. In another embodiment, the nucleic acid molecule includes SEQ ID NO:3 and nucleotides 1–106 of SEQ ID NO:1. In yet a further embodiment, the nucleic acid molecule includes SEQ ID NO:3 and nucleotides 1097–1327 of SEQ ID NO:1. In another preferred embodiment, the nucleic acid molecule consists of the nucleotide sequence shown in SEQ ID NO:1 or 3.

In another embodiment, a DHY nucleic acid molecule includes a nucleotide sequence encoding a protein having an amino acid sequence sufficiently identical to the amino acid sequence of SEQ ID NO:2. In a preferred embodiment, a DHY nucleic acid molecule includes a nucleotide sequence encoding a protein having an amino acid sequence at least 50%, 55%, 60%, 65%, 70%, 75%, 80%, 85%, 90%, 95%, 96%, 97%, 98%, 99% or more identical to the entire length of the amino acid sequence of SEQ ID NO:2.

In another preferred embodiment, an isolated nucleic acid molecule encodes the amino acid sequence of human DHY. In yet another preferred embodiment, the nucleic acid molecule includes a nucleotide sequence encoding a protein having the amino acid sequence of SEQ ID NO:2. In yet another preferred embodiment, the nucleic acid molecule is at leas 50–100, 100–150, 150–200, 200–250, 250–300, 300–350, 350–400, 400–450, 450–500, 500–550, 550–600, 600–650, 650–700, 700–750, 750–800, 800–850, 950–900, 900–950, 950–1000, 1000–1050, 1050–1100, 1100–1150, 1150–1200, 1200–1250, 1250–1300 or more nucleotides in length. In a further preferred embodiment, the nucleic acid molecule is at least 50–100, 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000, 1000–1050, 1050–1100, 1100–1150, 1150–1200, 1200–1250, 1250–1300 or more nucleotides in length and encodes a protein having a DHY activity (as described herein).

Another embodiment of the invention features nucleic acid molecules, preferably DHY nucleic acid molecules, which specifically detect DHY nucleic acid molecules relative to nucleic acid molecules encoding non-DHY proteins. For example, in one embodiment, such a nucleic acid molecule is at least 20–30, 3040,40–50, 50–100, 100–150, 150–200, 200–250, 250–300, 300–350, 350–400, 400–450, 450–500, 500–550, 550–600, 600–650, 650–700,700–750, 750–800, 800–850, 850–900, 900–950, 950–1000, 1000–1050, 1050–1100, 1100–1150, 1150–1200, 1200–1250, 1250–1300 or more nucleotides in length and hybridizes under stringent conditions to a nucleic acid molecule comprising the nucleotide sequence shown in SEQ ID NO:1, or a complement thereof.

In preferred embodiments, the nucleic acid molecules are at least 15 (e.g., 15 contiguous) nucleotides in length and hybridize under stringent conditions to the nucleotide molecule set forth in SEQ ID NO:1.

In other preferred embodiments, the nucleic acid molecule encodes a naturally occurring allelic variant of a polypeptide comprising the amino acid sequence of SEQ ID NO:2, wherein the nucleic acid molecule hybridizes to a nucleic acid molecule comprising SEQ ID NO:1 or 3, respectively, under stringent conditions.

Another embodiment of the invention provides an isolated nucleic acid molecule which is antisense to a DHY nucleic acid molecule, e.g., the coding strand of a DHY nucleic acid molecule.

Another aspect of the invention provides a vector comprising a DHY nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably a DHY protein, by culturing in a suitable medium, a host cell, e.g., a mammalian host cell such as a non-human mammalian cell, of the invention containing a recombinant expression vector, such that the protein is produced.

Another aspect of this invention features isolated or recombinant DHY proteins and polypeptides. In one embodiment, an isolated DHY protein includes at least one or more of the following domains: a transmembrane domain, a serine/threonine dehydratase pyridoxal-phosphate attachment site, a serine/threonine dehydratase domain, and/or pyridoxal phosphate-dependent lyase synthase domain.

In a preferred embodiment, a DHY protein includes at least one or more of the following domains: a transmembrane domain, a serine/threonine debydratase pyridoxal-phosphate attachment site, a serine/threonine dehydratase domain, and/or a pyridoxal phosphate-dependent lyase synthase domain, and has an amino acid sequence at least about 50%, 55%, 60%, 65%, 67%, 68%, 70%, 75%, 80%, 85%, 90%, 95%, 96%, 97%, 98%, 99% or more identical to the amino acid sequence of SEQ ID NO:2. In another preferred embodiment, a DHY protein includes at least one or more of the following domains: a transmembrane domain, a serine/threonine dehydratase pyridoxal-phosphate attachment site, a serine/threonine dehydratase domain, and/or a pyridoxal phosphate-dependent lyase synthase domain, and has a DHY activity (as described herein).

In yet another preferred embodiment, a DHY protein includes at least one or more of the following domains: a transmembrane domain, a serine/threonine dehydratase pyridoxal-phosphate attachment site, a serine/threonine dehydratase domain, and/or a pyridoxal phosphate-dependent lyase synthase domain, and is encoded by a nucleic acid molecule having a nucleotide sequence which hybridizes under stringent hybridization conditions to a nucleic acid molecule comprising the nucleotide sequence of SEQ ID NO:1 or 3.

In another embodiment, the invention features fragments of the protein having the amino acid sequence of SEQ ID NO:2, wherein the fragment comprises at least 15 amino acids (e.g., contiguous amino acids) of the amino acid sequence of SEQ ID NO:2. In another embodiment, a DHY protein has the amino acid sequence of SEQ ID NO:2.

In another embodiment, the invention features a DHY protein which is encoded by a nucleic acid molecule consisting of a nucleotide sequence at least about 50%, 55%, 60%, 65%, 70%, 75%, 80%, 85%, 90%, 95%, 96%, 97%, 98%, 99% or more identical to a nucleotide sequence of SEQ ID NO:1 or 3, or a complement thereof. This invention further features a DHY protein which is encoded by a nucleic acid molecule consisting of a nucleotide sequence which hybridizes under stringent hybridization conditions to a nucleic acid molecule comprising the nucleotide sequence of SEQ ID NO:1 or 3, or a complement thereof.

The proteins of the present invention or portions thereof, e.g., biologically active portions thereof, can be operatively linked to a non-DHY polypeptide (e.g., heterologous amino acid sequences) to form fusion proteins. The invention further features antibodies, such as monoclonal or polyclonal antibodies, that specifically bind proteins of the invention, preferably DHY proteins. In addition, the DHY proteins or biologically active portions thereof can be incorporated into pharmaceutical compositions, which optionally include pharmaceutically acceptable carriers.

In another aspect, the present invention provides a method for detecting the presence of a DHY nucleic acid molecule, protein, or polypeptide in a biological sample by contacting the biological sample with an agent capable of detecting a DHY nucleic acid molecule, protein, or polypeptide such that the presence of a DHY nucleic acid molecule, protein or polypeptide is detected in the biological sample.

In another aspect, the present invention provides a method for detecting the presence of DHY activity in a biological sample by contacting the biological sample with an agent capable of detecting an indicator of DHY activity such that the presence of DHY activity is detected in the biological sample.

In another aspect, the invention provides a method for modulating DHY activity comprising contacting a cell capable of expressing DHY with an agent that modulates DHY activity such that DHY activity in the cell is modulated. In one embodiment, the agent inhibits DHY activity. In another embodiment, the agent stimulates DHY activity. In one embodiment, the agent is an antibody that specifically binds to a DHY protein. In another embodiment, the agent modulates expression of DHY by modulating transcription of a DHY gene or translation of a DHY mRNA. In yet another embodiment, the agent is a nucleic acid molecule having a nucleotide sequence that is antisense to the coding strand of a DHY mRNA or a DHY gene.

In one embodiment, the methods of the present invention are used to treat a subject having a disorder characterized by aberrant or unwanted DHY protein or nucleic acid expression or activity by administering an agent which is a DHY modulator to the subject. In one embodiment, the DHY modulator is a DHY protein. In another embodiment the DHY modulator is a DHY nucleic acid molecule. In yet another embodiment, the DHY modulator is a peptide, peptidomimetic, or other small molecule. In a preferred embodiment, the disorder characterized by aberrant or unwanted DHY protein or nucleic acid expression is a dehydratase-associated disorder, e.g., a CNS disorder, a cardiovascular disorder, a muscular disorder, or a cell proliferation, growth, differentiation, or migration disorder.

The present invention also provides diagnostic assays for identifying the presence or absence of a genetic alteration characterized by at least one of (i) aberrant modification or mutation of a gene encoding a DHY protein; (ii) misregulation of the gene; and (iii) aberrant post-translational modification of a DHY protein, wherein a wild-type form of the gene encodes a protein with a DHY activity.

In another aspect the invention provides methods for identifying a compound that binds to or modulates the activity of a DHY protein, by providing an indicator composition comprising a DHY protein having DHY activity, contacting the indicator composition with a test compound, and determining the effect of the test compound on DHY activity in the indicator composition to identify a compound that modulates the activity of a DHY protein.

Other features and advantages of the invention will be apparent from the following detailed description and claims.

BRIEF DESCRIPTION OF THE DRAWINGS

FIGS. 1A–B depicts the cDNA sequence and predicted amino acid sequence of human DHY (clone Fbh26335). The nucleotide sequence corresponds to nucleic acids 1 to 1327 of SEQ ID NO:1. The amino acid sequence corresponds to amino acids 1 to 329 of SEQ ID NO:2. The coding region without the 3' untranslated region of the human DHY gene is shown in SEQ ID NO:3.

FIG. 2 depicts a hydrophobicity analysis of the human DHY protein.

FIG. 3 depicts the results of a search which was performed against the MEMSAT database and which resulted in the identification of four "transmembrane domains" in the human DHY protein (SEQ ID NO:2).

FIG. 4 depicts the results of a search which was performed against the ProSite database and which resulted in the identification of a "serine/threonine dehydratase pyridoxal-phosphate attachment site" in the human DHY protein (SEQ ID NO:2).

FIG. 5 depicts the results of a search which was performed against the HMM database and which resulted in the identification of a "serine/threonine dehydratase domain" in the human DHY protein.

FIG. 6 depicts the results of a search which was performed against the ProDom database and which resulted in the identification of a "pyridoxal phosphate-dependent lyase synthase domain" in the human DHY protein (SEQ ID NO:2).

DETAILED DESCRIPTION OF THE INVENTION

The present invention is based, at least in part, on the discovery of novel molecules, referred to herein as "dehydratase" or "DHY" nucleic acid and protein molecules, which are novel members of a family of enzymes possessing dehydratase activity. These novel molecules are capable of deaminating serine or threonine to pyruvate or 2-oxobutyrate, respectively, by catalyzing a two-step reaction of dehydration of the amino acid, followed by hydrolysis of the resulting imine. These novel molecules may thus play a role in or function in a variety of cellular processes, e.g., cellular proliferation, growth, differentiation, migration, and inter- or intra-cellular communication.

As used herein, the term "dehydratase" includes a molecule which is involved in the metabolism and catabolism of biochemical molecules necessary for energy metabolism, for intra- or intercellular signaling, and for metabolism or catabolism of metabolically important biomolecules. Typically, dehydratases are involved in the deamination of amino acids, e.g., serine or threonine. Examples of dehydratases include serine and threonine dehydratases. Thus, the DHY molecules of the present invention provide novel diagnostic targets and therapeutic agents to control dehydratase-associated disorders.

As used herein, a "dehydratase-associated disorder" includes a disorder, disease or condition which is caused or characterized by a misregulation (e.g., downregulation or upregulation) of dehydratase activity. Misregulation of dehydratase activity can result in the overproduction or lack of production of one or more amino acids or biologically important metabolic precursor molecules (e.g., pyruvate or 2-oxobutyrate), and, by extension, aberrant metabolite, energy molecules, and/or protein production in the cell as a whole. Proteins produced by the cell not only include those involved in normal cellular functioning (e.g., enzymes, receptors, chaperoning, and transcription factors), but also important signaling molecules (e.g., growth factors, cytokines, and neuropeptides). Dehydratase-associated disorders, therefore, can detrimentally affect cellular functions such as cellular proliferation, growth, differentiation, or migration, inter- or intra-cellular communication; and tissue function, such as cardiac function or musculoskeletal function. Examples of dehydratase-associated disorders include CNS disorders such as cognitive and neurodegenerative disorders, examples of which include, but are not limited to, Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, and Jakob-Creutzfieldt disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Further CNS-related disorders include, for example, those listed in the American Psychiatric Association's Diagnostic and Statistical manual of Mental Disorders (DSM), the most current version of which is incorporated herein by reference in its entirety.

Further examples of dehydratase-associated disorders include cardiac-related disorders. Cardiovascular system disorders in which the DHY molecules of the invention may be directly or indirectly involved include arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation, Jervell syndrome, Lange-Nielsen syndrome, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia. DHY-mediated or related disorders also include disorders of the musculoskeletal system such as paralysis and muscle weakness, e.g., ataxia, myotonia, and myokymia.

Dehydratase disorders also include cellular proliferation, growth, differentiation, or migration disorders. Cellular proliferation, growth, differentiation, or migration disorders include those disorders that affect cell proliferation, growth, differentiation, or migration processes. As used herein, a "cellular proliferation, growth, differentiation, or migration process" is a process by which a cell increases in number, size or content, by which a cell develops a specialized set of characteristics which differ from that of other cells, or by which a cell moves closer to or further from a particular location or stimulus. The DHY molecules of the present invention are involved in signal transduction mechanisms, which are known to be involved in cellular growth, differentiation, and migration processes. Thus, the DHY molecules may modulate cellular growth, differentiation, or migration, and may play a role in disorders characterized by aberrantly regulated growth, differentiation, or migration. Such disorders include cancer, e.g., carcinoma, sarcoma, or leukemia; tumor angiogenesis and metastasis; skeletal dysplasia; hepatic disorders; and hematopoietic and/or myeloproliferative disorders.

DHY-associated or related disorders also include disorders affecting tissues in which DHY protein is expressed.

As used herein, a "dehydratase-mediated activity" includes an activity which involves the deamination of one or more amino acids, e.g., threonine or serine. Dehydratase-mediated activities include the production of biochemical molecules necessary for energy metabolism, for intra- or intercellular signaling (e.g., the production of growth factors), and for metabolism or catabolism of metabolically important biomolecules (e.g., isoleucine and protein production).

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin, e.g., monkey proteins. Members of a family may also have common functional characteristics.

For example, the family of DHY proteins comprises at least one "transmembrane domain". As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al., (1996) *Annual Rev. Neurosci.* 19: 235–263, the contents of which are incorporated herein by reference. Amino acid residues 67–83, 167–187, 270–288, and 295–311 of the native DHY protein are predicted to comprise transmembrane domains (see FIG. 3). Accordingly, DHY proteins having at least 50–60% homology, preferably about 60–70%, more preferably about 70–80%, or about 80–90% homology with a transmembrane domain of human DHY are within the scope of the invention.

In another embodiment, a DHY molecule of the present invention is identified based on the presence of a "serine/threonine dehydratase pyridoxal-phosphate attachment site" in the protein or corresponding nucleic acid molecule. As used herein, the term "serine/threonine dehydratase pyridoxal-phosphate attachment site" includes a protein domain having an amino acid sequence of about 10–20 amino acid residues. Preferably, a serine/threonine dehydratase pyridoxal-phosphate attachment site has about 14 residues and the following consensus sequence: [DESH]-x (4, 5)-[STVG]-x-[AS]-[FYI]-K-[DLIFSA]-[RVMF]-[GA]-[LIVMGA] (SEQ ID NO:4) (Datta et al. (1987) *Proc. Natl. Acad. Sci. USA* 84:393–397; and Ogawa et al. (1989) *Biochim. Biophys. Acta* 996:139–141). To identify the presence of a serine/threonine dehydratase pyridoxal-phosphate attachment site in a DHY protein, and make the determination that a protein of interest has a particular profile, the amino acid sequence of the protein may be searched against a database of known protein domains (e.g., the ProSite database). The serine/threonine dehydratase pyridoxal-phosphate attachment site has been assigned ProSite accession number PS00165 (http://www.expasy.ch/cgi-bin/prosite-search-ac?PS00165). A search was performed against the ProSite database resulting in the identification of a serine/threonine dehydratase pyridoxal-phosphate attachment site in the amino acid sequence of human DHY (SEQ ID NO:2) at about residues 39–52 of SEQ ID NO:2. The results of the search are set forth in FIG. 4.

In another embodiment, a DHY molecule of the present invention is identified based on the presence of an "serine/threonine dehydratase domain" in the protein or corresponding nucleic acid molecule. As used herein, the term "serine/threonine dehydratase domain" includes a protein domain having an amino acid sequence of about 200–400 amino acid residues and a bit score of about 50, 60, 70, 80, 90, 100, 110, 120, 130, 140, 150, 160, 170, 180, 190, 200, 210, or 220 or more. Preferably, a serine/threonine dehydratase domain includes at least about 250–350, or more preferably about 301 amino acid residues, and a bit score of at least 229. To identify the presence of a serine/threonine dehydratase domain in a DHY protein, and make the determination that a protein of interest has a particular profile, the amino acid sequence of the protein may be searched against a database of known protein domains (e.g., the HMM database). A search was performed against the HMM database resulting in the identification of a serine/threonine dehydratase domain in the amino acid sequence of human DHY (SEQ ID NO:2) at about residues 11–311 of SEQ ID NO:2. The results of the search are set forth in FIG. 5.

In another embodiment, a DHY molecule of the present invention is identified based on the presence of a "pyridoxal phosphate-dependent lyse synthase domain" in the protein or corresponding nucleic acid molecule. As used herein, the term "pyridoxal phosphate-dependent lyse synthase domain" includes a protein domain having an amino acid sequence of about 200–300 amino acid residues and having a bit score for the alignment of the sequence to the pyridoxal phosphate-dependent lyse synthase domain of at least 10, 20, 30, 40, 50, 60, 70, 80 or higher. Preferably, a pyridoxal phosphate-dependent lyse synthase domain includes at least about 240–275, or more preferably about 265 amino acid residues, and has a bit score for the alignment of the sequence to the pyridoxal phosphate-dependent lyase synthase domain of at least 88. The pyridoxal phosphate-dependent lyase synthase domain has been assigned Pro-Dom entry 206. To identify the presence of a pyridoxal phosphate-dependent lyase synthase domain in a DHY protein, and to make the determination that a protein of interest has a particular profile, the amino acid sequence of the protein may be searched against a database of known protein domains (e.g., the ProDom database) using the default parameters (available at http://www.toulouse.inra.fr/prodom.html). A search was performed against the ProDom database resulting in the identification of a pyridoxal phosphate-dependent lyase synthase domain in the amino acid sequence of human DHY (SEQ ID NO:2) at about residues 18–282 of SEQ ID NO:2. The results of the search are set forth in FIG. 6.

In a preferred embodiment, the DHY molecules of the invention include at least one or more of the following domains: a transmembrane domain, a serine/threonine dehydratase pyridoxal-phosphate attachment site, a serine/threonine dehydratase domain, and/or a pyridoxal phosphate-dependent lyase synthase domain.

Isolated proteins of the present invention, preferably DHY proteins, have an amino acid sequence sufficiently identical to the amino acid sequence of SEQ ID NO:2, or are encoded by a nucleotide sequence sufficiently identical to SEQ ID NO:1 or 3. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% homology and share a common functional activity are defined herein as sufficiently identical.

As used interchangeably herein, an "DHY activity", "biological activity of DHY" or "functional activity of DHY", refers to an activity exerted by a DHY protein, polypeptide or nucleic acid molecule on a DHY responsive cell or tissue, or on a DHY protein substrate, as determined in vivo, or in vitro, according to standard techniques. In one embodiment, a DHY activity is a direct activity, such as an association with a DHY-target molecule. As used herein, a "target molecule" or "binding partner" is a molecule with which a DHY protein binds or interacts in nature, such that DHY-mediated function is achieved. A DHY target molecule can be a non-DHY molecule or a DHY protein or polypeptide of the present invention (e.g., pyridoxal-5'-phosphate). In an exemplary embodiment, a DHY target molecule is a DHY ligand (e.g., serine or threonine). Alternatively, a DHY activity is an indirect activity, such as a cellular signaling activity mediated by interaction of the DHY protein with a DHY ligand. The biological activities of DHY are described herein. For example, the DHY proteins of the present invention can have one or more of the following activities: 1) modulate metabolism and catabolism of biochemical molecules necessary for energy production or storage (e.g., amino acids, such as serine or threonine); 2) modulate intra- or intercellular signaling; 3) modulate metabolism or catabolism of metabolically important biomolecules; 4) modulate cellular growth and differentiation; 5) modulate cellular proliferation; and 6) modulate production of growth factors and cytokines.

Accordingly, another embodiment of the invention features isolated DHY proteins and polypeptides having a DHY activity. Other preferred proteins are DHY proteins having one or more of the following domains: a transmembrane domain, a serine/threonine dehydratase pyridoxal-phosphate attachment site, a serine/threonine dehydratase domain, and/or a pyridoxal phosphate-dependent lyase synthase domain and, preferably, a DHY activity.

Additional preferred proteins have one or more of the following domains: a transmembrane domain, a serine/threonine dehydratase pyridoxal-phosphate attachment site, a serine/threonine dehydratase domain, and/or a pyridoxal phosphate-dependent lyase synthase domain, and are, preferably, encoded by a nucleic acid molecule having a nucleotide sequence which hybridizes under stringent hybridization conditions to a nucleic acid molecule comprising the nucleotide sequence of SEQ ID NO:1 or 3.

The nucleotide sequence of the isolated human DHY cDNA and the predicted amino acid sequence of the human DHY polypeptide are shown in FIG. 1 and in SEQ ID NOs:1 and 2, respectively.

The human DHY gene, which is approximately 1327 nucleotides in length, encodes a protein having a molecular weight of approximately 36.2 kD and which is approximately 329 amino acid residues in length.

Various aspects of the invention are described in further detail in the following subsections:

I. Isolated Nucleic Acid Molecules

One aspect of the invention pertains to isolated nucleic acid molecules that encode DHY proteins or biologically active portions thereof, as well as nucleic acid fragments sufficient for use as hybridization probes to identify DHY-encoding nucleic acid molecules (e.g., DHY mRNA) and fragments for use as PCR primers for the amplification or mutation of DHY nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated DHY nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1 or 3, or a portion thereof, can be isolated sing standard molecular biology techniques and the sequence information provided herein. Using all or portion of the nucleic acid sequence of SEQ ID NO:1 or 3 as a hybridization probe, DHY nucleic acid molecules can be isolated using standard hybridization and cloning techniques (e.g., as described in Sambrook, J., Fritsh, E. F., and Miniatis, T. *Molecular Cloning: A Laboratory Manual. 2nd ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1 or 3 can be isolated by the polymerase chain reaction (PCR) using synthetic oligonucleotide primers designed based upon the sequence of SEQ ID NO:1 or 3.

A nucleic acid of the invention can be amplified using cDNA, mRNA or, alternatively, genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to DHY nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1 or 3. This cDNA may comprise sequences encoding the human DHY protein (i.e., "the coding region", from nucleotides 107–1096), as well as 5' untranslated sequences (nucleotides 1–106) and 3' untranslated sequences (nucleotides 1097–1327) of SEQ ID NO:1. Alternatively, the nucleic acid molecule can comprise only the coding region of SEQ ID NO:1 (e.g., nucleotides 107–1096, corresponding to SEQ ID NO:3).

In another preferred embodiment, an isolated nucleic acid molecule of the invention comprises a nucleic acid molecule which is a complement of the nucleotide sequence shown in SEQ ID NO:1 or 3, or a portion of any of these nucleotide sequences. A nucleic acid molecule which is complementary to the nucleotide sequence shown in SEQ ID NO:1 or 3, is one which is sufficiently complementary to the nucleotide sequence shown in SEQ ID NO:1 or 3 such that it can hybridize to the nucleotide sequence shown in SEQ ID NO:1 or 3, respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 96%, 97%, 98%, 99% or more identical to the entire length of the nucleotide sequence show in SEQ ID NO:1 or 3, or a portion of any of these nucleotide sequences.

Moreover, the nucleic acid molecule of the invention can comprise only a portion of the nucleic acid sequence of SEQ ID NO:1 or 3, for example, a fragment which can be used as a probe or primer or a fragment encoding a portion of a DHY protein, e.g., a biologically active potion of a DHY protein. The nucleotide sequences determined from the cloning of the DHY genes allow for the generation of probes and primers designed for use in identifying and/or cloning other DHY family members, as well as DHY homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1 or 3 of an anti-sense sequence of SEQ ID NO:1 or 3 or of a naturally occurring allelic variant or mutant of SEQ ID NO:1 or 3. In one embodiment, a nucleic acid molecule of the present invention comprises a nucleotide sequence which is greater than 50–100, 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000, 1000–1050, 1050–1100, 1100–1150, 1150–1200, 1200–1250, 1250–1300 or more nucleotides in length and hybridizes under stringent hybridization conditions to a nucleic acid molecule of SEQ ID NO:1 or 3.

Probes based on the DHY nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a DHY protein, such as by measuring a level of a DHY-encoding nucleic acid in a sample of cells from a subject e.g., detecting DHY mRNA levels or determining whether a genomic DHY gene has been mutated or deleted.

A nucleic acid fragment encoding a "biologically active portion of a DHY protein" can be prepared by isolating a portion of the nucleotide sequence of SEQ ID NO:1 or 3 which encodes a polypeptide having a DHY biological activity (the biological activities of the DHY proteins are described herein), expressing the encoded portion of the DHY protein (e.g., by recombinant expression in vitro) and assessing the activity of the encoded portion of the DHY protein.

The invention further encompasses nucleic acid molecules that differ from the nucleotide sequence shown in SEQ ID NO:1 or 3 due to degeneracy of the genetic code and thus encode the same DHY proteins as those encoded by the nucleotide sequence shown in SEQ ID NO:1 or 3. In another embodiment, an isolated nucleic acid molecule of the invention has a nucleotide sequence encoding a protein having an amino acid sequence shown in SEQ ID NO:2.

In addition to the DHY nucleotide sequences shown in SEQ ID NO:1 or 3, it will be appreciated by those skilled in the art that DNA sequence polymorphisms that lead to changes in the ado acid sequences of the DHY proteins may within a population (e.g., the human population). Such genetic polymorphism in the DHY genes may exist among individuals within a population due to natural allelic variation. As used herein, the terms "gene" and "recombinant gene" refer to nucleic acid molecules which include an open reading frame encoding a DHY proteins preferably a mammalian DHY protein, and can further include non-coding regulatory sequences, and introns.

Allelic variants of human DHY include both functional and non-functional DHY proteins. Functional allelic variants are naturally occurring amino acid sequence variants of the human DHY protein that maintain the ability to bind a DHY ligand or substrate and/or modulate cell proliferation and/or migration mechanisms. Functional allelic variants will typically contain only conservative substitution of one or more amino acids of SEQ ID NO:2, or substitution, deletion or insertion of non-critical residues in non-critical regions of the protein.

Non-functional allelic variants are naturally occurring amino acid sequence variants of the human DHY protein that do not have the ability to either bind a DHY ligand and/or modulate any of the DHY activities described herein. Non-functional allelic variants will typically contain a non-conservative substitution, a deletion, or insertion or premature truncation of the amino acid sequence of SEQ ID NO:2, or a substitution, insertion or deletion in critical residues or critical regions of the protein.

The present invention further provides non-human orthologues of the human DHY protein. Orthologues of the human DHY protein are proteins that are isolated from non-human organisms and possess the same DHY ligand binding and/or modulation of membrane excitability activities of the human DHY protein. Orthologues of the human DHY protein can readily be identified as comprising an amino acid sequence that is substantially identical to SEQ ID NO:2.

Moreover, nucleic acid molecules encoding other DHY family members and, thus, which have a nucleotide sequence which differs from the DHY sequences of SEQ ID NO:1 or 3 are intended to be within the scope of the invention. For example, another DHY cDNA can be identified based on he nucleotide sequence of human DHY. Moreover, nucleic acid molecules encoding DHY proteins from different species, and which, thus, have a nucleotide sequence which differs from the DHY sequences of SEQ ID NO:1 or 3 are intended to be within the scope of the invention. For example, a mouse DHY cDNA can be identified based on the nucleotide sequence of a human DHY.

Nucleic acid molecules corresponding to natural allelic variants and homologues of the DHY cDNAs of the invention can be isolated based on their homology to the DHY nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the DHY cDNAs of the invention can further be isolated by mapping to the same chromosome or locus as the DHY gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1 or 3. In other embodiment, the nucleic acid is at least 50–100, 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000, 1000–1050, 1050–1100, 1100–1150, 1150–1200, 1200–1250, 1250–1300 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4×sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6($\log_{10}$[Na$^+$])+0.41(%G+C)−(600/N), where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M NaH$_2$PO$_4$, 7% SDS at about 65° C., followed by one or more washes at 0.02M NaH$_2$PO$_4$, 1% SDS at 65° C., see e.g., Church and Gilbert (1984) *Proc. Natl. Acad. Sci. USA* 81:1991–1995, (or alternatively 0.2×SSC, 1% SDS).

Preferably, an isolated nucleic acid molecule of the invention that hybridizes under stringent conditions to the sequence of SEQ ID NO:1 or 3, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the DHY sequences that may exist in the population, the skilled artisan will further appreciate that changes can be introduced by mutation into the nucleotide sequences of SEQ ID NO:1 or 3, thereby leading to changes in the amino acid sequence of the encoded DHY proteins, without altering the functional ability of the DHY proteins. For example, nucleotide substitutions leading to amino acid substitutions at "non-essential" amino acid residues can be made in the sequence of SEQ ID NO:1 or 3. A "non-essential" amino acid residue is a residue that can be altered from the wild-type sequence of DHY (e.g., the sequence of SEQ ID NO:2) without altering the biological activity, whereas an "essential" amino acid residue is required for biological activity. For example, amino acid residues that are conserved among the DHY proteins of the present invention, e.g., those present in a transmembrane domain, are predicted to be particularly unamenable to alteration. Furthermore, additional amino acid residues that are conserved between the DHY proteins of the present invention and other members of the DHY family are not likely to be amenable to alteration.

Accordingly, another aspect of the invention pertains to nucleic acid molecules encoding DHY proteins that contain changes in amino acid residues that are not essential for activity. Such DHY proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95%, 96%, 97%, 98%, 99% or more identical to SEQ ID NO:2.

An isolated nucleic acid molecule encoding a DHY protein identical to the protein of SEQ ID NO:2 can be creased by introducing one or more nucleotide substitutions, additions or deletions into the nucleotide sequence of SEQ ID NO:1 or 3 such that one or more amino acid substitutions, additions or deletions are introduced into the encoded protein. Mutations can be introduced into SEQ ID NO:1 or 3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutarine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a DHY protein is preferably replaced wit another amino acid residue from the same side chain family. Alternatively, in another embodiment, mutations can be introduced randomly along all or part of a DHY coding sequence, such as by saturation mutagenesis, and the resultant mutants can be screened for DHY biological activity to identify mutants that retain activity. Following mutagenesis of SEQ ID NO:1 or 3, the encoded protein can be expressed recombinantly and the activity of the protein can be determined.

In a preferred embodiment, a mutant DHY protein can be assayed for the ability to metabolize or catabolize biochemical molecules necessary for energy production or storage, permit intra- or intercellular signaling, metabolize or catabolize metabolically important biomolecules, and to detoxify potentially harmful compounds.

In addition to the nucleic acid molecules encoding DHY proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire DHY coding strand, or to only a portion thereof. In one embodiment, an antisense nucleic acid molecule is antisense to a "coding region" of the coding strand of a nucleotide sequence encoding a DHY. The term "coding region" refers to the region of the nucleotide sequence comprising codons which are translated into amino acid residues (e.g., the coding region of human DHY corresponds to SEQ ID NO:3). In another embodiment, the antisense nucleic acid molecule is antisense to a "noncoding region" of the coding strand of a nucleotide sequence encoding DHY. The term "noncoding region" refers to 5' and 3' sequences which flank the coding region that are not translated into amino acids (i.e., also referred to as 5' and 3' untranslated regions).

Given the coding strand sequences encoding DHY disclosed herein (e.g., SEQ ID NO:3), antisense nucleic acids of the invention can be designed according to the rules of Watson and Crick base pairing. The antisense nucleic acid molecule can be complementary to the entire coding region of DHY mRNA, but more preferably is an oligonucleotide which is antisense to only a portion of the coding or noncoding region of DHY mRNA. For example, the antisense oligonucleotide can be complementary to the region surrounding the translation start site of DHY mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a DHY protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense.nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleavig a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave DHY mRNA transcripts to thereby inhibit translation of DHY mRNA. A ribozyme having specificity for a DHY-encoding nucleic acid can be designed based upon the nucleotide sequence of a DHY cDNA disclosed herein (i.e., SEQ ID NO:1 or 3). For example, a derivative of a Tetrahymena L-19 IVS RNA can be constructed in which the nucleotide sequence of the active site is complementary to the nucleotide sequence to be cleaved in a DHY-encoding mRNA. See, e.g, Cech et al. U.S. Pat. No. 4,987,071; and Cech et al. U.S. Pat. No. 5,116,742. Alternatively, DHY mRNA can be used to select a catalytic RNA having a specific ribonuclease activity from a pool of RNA molecules. See, e.g., Bartel, D. and Szostak, J. W. (1993) *Science* 261:1411–1418.

Alternatively, DHY gene expression can be inhibited by targeting nucleotide sequences complementary to the regulatory region of the DHY (e.g., the DHY promoter and/or enhancers; e.g., nucleotides 1–106 of SEQ ID NO:1) to form triple helical structures that prevent transcription of the DHY gene in target cells. See generally, Helene, C. (1991) *Anticancer Drug Des.* 6(6): 569–84; Helene, C. et al. (1992) *Ann. N.Y. Acad. Sci.* 660:27–36; and Maher, L.J. (1992) *Bioassays* 14(12):807–15.

In yet another embodiment, the DHY nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670–675.

PNAs of DHY nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of DHY nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of DHY can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of DHY nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors, in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988)

*Pharm. Res.* 5:539–549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous DHY gene within a cell line or microorganism may be modified by inserting a heterologous DNA regulatory element into the genome of a stable cell line or cloned microorganism such that the inserted regulatory element is operatively linked with the endogenous DHY gene. For example, an endogenous DHY gene which is normally "transcriptionally silent", i.e., a DHY gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous DHY gene may be activated by insertion of a promiscuous regulatory element that works across cell types.

A heterologous regulatory element may be inserted into a stable cell line or cloned microorganism, such that it is operatively linked with an endogenous DHY gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated DHY Proteins and Anti-DHY Antibodies

One aspect of the invention pertains to isolated DHY proteins, and biologically active portions thereof, as well as polypeptide fragments suitable for use as immunogens to raise anti-DHY antibodies. In one embodiment, native DHY proteins can be isolated from cells or tissue sources by an appropriate purification scheme using standard protein purification techniques. In another embodiment, DHY proteins are produced by recombinant DNA techniques. Alternative to recombinant expression, a DHY protein or polypeptide can be synthesized chemically using standard peptide synthesis techniques.

An "isolated" or "purified" protein or biologically active portion thereof is substantially free of cellular material or other contaminating proteins from the cell or tissue source from which the DHY protein is derived, or substantially free from chemical precursors or other chemicals when chemically synthesized. The language "substantially free of cellular material" includes preparations of DHY protein in which the protein is separated from cellular components of the cells from which it is isolated or recombinantly produced. In one embodiment, the language "substantially free of cellular material" includes preparations of DHY protein having less than about 30% (by dry weight) of non-DHY protein (also referred to herein as a "contaminating protein"), more preferably less than about 20% of non-DHY protein, still more preferably less than about 10% of non-DHY protein, and most preferably less than about 5% non-DHY protein. When the DHY protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of DHY protein in which the protein is separated from chemical precursors or other chemicals which are involved in the synthesis of the protein. In one embodiment, the language "substantially free of chemical precursors or other chemicals" includes preparations of DHY protein having less than about 30% (by dry weight) of chemical precursors or non-DHY chemicals, more preferably less than about 20% chemical precursors or non-DHY chemicals, still more preferably less than about 10% chemical precursors or non-DHY chemicals, and most preferably less than about 5% chemical precursors or non-DHY chemicals.

As used herein, a "biologically active portion" of a DHY protein includes a fragment of a DHY protein which participates in an interaction between a DHY molecule and a non-DHY molecule. Biologically active portions of a DHY protein include peptides comprising amino acid sequences sufficiently identical to or derived from the amino acid sequence of the DHY protein, e.g., the amino acid sequence shown in SEQ ID NO:2, which include less amino acids than the full length DHY proteins, and exhibit at least one activity of a DHY protein. Typically, biologically active portions comprise a domain or motif with at least one activity of the DHY protein, e.g., modulating membrane excitability. A biologically active portion of a DHY protein can be a polypeptide which is, for example, 25, 50, 75, 100, 125, 150, 175, 200, 250, 300 or more amino acids in length. Biologically active portions of a DHY protein can be used as targets for developing agents which modulate a DHY mediated activity, e.g., a proliferative response.

In one embodiment, a biologically active portion of a DHY protein comprises at least one transmembrane domain. It is to be understood that a preferred biologically active portion of a DHY protein of the present invention may contain at least one transmembrane domain and one or more of the following domains: a transmembrane domain, a serine/threonine dehydratase pyridoxal-phosphate attachment site, a serine/threonine dehydratase domain, and/or a pyridoxal phosphate-dependent lyase synthase domain. Moreover, other biologically active portions, in which other regions of the protein are deleted, can be prepared by recombinant techniques and evaluated for one or more of the functional activities of a native DHY protein.

In a preferred embodiment, the DHY protein has an amino acid sequence shown in SEQ ID NO:2. In other embodiments, the DHY protein is substantially identical to SEQ ID NO:2, and retains the functional activity of the protein of SEQ ID NO:2, yet differs in amino acid sequence due to natural allelic variation or mutagenesis, as described in detail in subsection I above. Accordingly, in another embodiment, the DHY protein is a protein which comprises an amino acid sequence at least about 50%, 55%, 60%, 65%, 70%, 75%, 80%, 85%, 90%, 95%, 96%, 97%, 98%, 99% or more identical to SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the DHY amino acid sequence of SEQ ID NO:2 having 329 amino acid residues, at least 50, preferably at least 100, more preferably at least 150, even more preferably at least 200, and even more preferably at least 300 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.*, 4:11–17 (1988)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to DHY nucleic acid molecules of the invention. BLAST protein searches can be performed with the XBLAST program, score=100, wordlength=3 to obtain amino acid sequences homologous to DHY protein molecules of the invention. To obtain gapped alignments for comparison purposes, Gapped BLAST can be utilized as described in Altschul et al., (1997) *Nucleic Acids Res.* 25(17) :3389–3402. When utilizing BLAST and Gapped BLAST programs, the default parameters of the respective programs (e.g., XBLAST and NBLAST) can be used. See http://www.ncbi.nlm.nih.gov.

The invention also provides DHY chimeric or fusion proteins. As used herein, a DHY "chimeric protein" or "fusion protein" comprises a DHY polypeptide operatively linked to a non-DHY polypeptide. An "DHY polypeptide" refers to a polypeptide having an amino acid sequence corresponding to a DHY molecule, whereas a "non-DHY polypeptide" refers to a polypeptide having an amino acid sequence corresponding to a protein which is not substantially homologous to the DHY protein, e.g., a protein which is different from the DHY protein and which is derived from the same or a different organism. Within a DHY fusion protein the DHY polypeptide can correspond to all or a portion of a DHY protein. In a preferred embodiment, a DHY fusion protein comprises at least one biologically active portion of a DHY protein. In another preferred embodiment, a DHY fusion protein comprises at least two biologically active portions of a DHY protein. Within the fusion protein, the term "operatively linked" is intended to indicate that the DHY polypeptide and the non-DHY polypeptide are fused in-frame to each other. The non-DHY polypeptide can be fused to the N-terminus or C-terminus of the DHY polypeptide.

For example, in one embodiment, the fusion protein is a GST-DHY fusion protein in which the DHY sequences are fused to the C-terminus of the GST sequences. Such fusion proteins can facilitate the purification of recombinant DHY.

In another embodiment, the fusion protein is a DHY protein containing a heterologous signal sequence at its N-terminus. In certain host cells (e.g., mammalian host cells), expression and/or secretion of DHY can be increased through use of a heterologous signal sequence.

The DHY fusion proteins of the invention can be incorporated into pharmaceutical compositions and administered to a subject in vivo. The DHY fusion proteins can be used to affect the bioavailability of a DHY substrate. Use of DHY fusion proteins may be useful therapeutically for the treatment of disorders caused by, for example, (i) aberrant modification or mutation of a gene encoding a DHY protein; (ii) mis-regulation of the DHY gene; and (iii) aberrant post-translational modification of a DHY protein.

Moreover, the DRY-fusion proteins of the invention can be used as immunogens to produce anti-DHY antibodies in a subject, to purify DHY ligands and in screening assays to identify molecules which inhibit the interaction of DHY with a DHY substrate.

Preferably, a DHY chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A DHY-encoding nucleic acid can be cloned into such an expression vector such that the fusion moiety is linked in-frame to the DHY protein.

The present invention also pertains to variants of the DHY proteins which function as either DHY agonists (mimetics) or as DHY antagonists. Variants of the DHY proteins can be generated by mutagenesis, e.g., discrete point mutation or truncation of a DHY protein. An agonist of the DHY proteins can retain substantially the same, or a subset, of the biological activities of the naturally occurring form of a DHY protein. An antagonist of a DHY protein can inhibit one or more of the activities of the naturally occurring form of the DHY protein by, for example, competitively modulating a DHY-mediated activity of a DHY protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the DHY protein.

In one embodiment, variants of a DHY protein which function as either DHY agonists (mimetics) or as DHY antagonists can be identified by screening combinatorial libraries of mutants, e.g., truncation mutants, of a DHY protein for DHY protein agonist or antagonist activity. In one embodiment, a variegated library of DHY variants is generated by combinatorial mutagenesis at the nucleic acid level and is encoded by a variegated gene library. A variegated library of DHY variants can be produced by, for example, enzymatically ligating a mixture of synthetic oligonucleotides into gene sequences such that a degenerate set of potential DHY sequences is expressible as individual polypeptides, or alternatively, as a set of larger fusion proteins (e.g., for phage display) containing the set of DHY sequences therein. There are a variety of methods which can be used to produce libraries of potential DHY variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential DHY sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a DHY protein coding sequence can be used to generate a variegated population of DHY fragments for screening and subsequent selection of variants of a DHY protein. In one embodiment, a library of coding sequence fragments can be generated by treating a double stranded PCR fragment of a DHY coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the DHY protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of DHY proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify DHY variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated DHY library. For example, a library of expression vectors can be transfected into a cell line, e.g., a neuronal cell line, which ordinarily responds to a DHY ligand in a particular DHY ligand-dependent manner. The transfected cells are then contacted with a DHY ligand and the effect of expression of the mutant on, e.g., membrane excitability of DHY can be detected. Plasmid DNA can then be recovered from the cells which score for inhibition, or alternatively, potentiation of signaling by the DHY ligand, and the individual clones further characterized.

An isolated DHY protein, or a portion or fragment thereof, can be used as an immunogen to generate antibodies that bind DHY using standard techniques for polyclonal and monoclonal antibody preparation. A full-length DHY protein can be used or, alternatively, the invention provides antigenic peptide fragments of DHY for use as immunogens. The antigenic peptide of DHY comprises at least 8 amino acid residues of the amino acid sequence shown in SEQ ID NO:2 and encompasses an epitope of DHY such that an antibody raised against the peptide forms a specific immune complex with the DHY protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of DHY that are located on the surface of the protein, e.g., hydrophilic regions, as well as regions with high antigenicity (see, for example, FIG. 2).

A DHY immunogen typically is used to prepare antibodies by immunizing a suitable subject, (e.g., rabbit, goat, mouse or other mammal) with the immunogen. An appropriate immunogenic preparation can contain, for example, recombinantly expressed DHY protein or a chemically synthesized DHY polypeptide. The preparation can further include an adjuvant, such as Freund's complete or incomplete adjuvant, or similar immunostimulatory agent. Immunization of a suitable subject with an immunogenic DHY preparation induces a polyclonal anti-DHY antibody response.

Accordingly, another aspect of the invention pertains to anti-DHY antibodies. The term "antibody" as used herein refers to immunoglobulin molecules and immunologically active portions of immunoglobulin molecules, i.e., molecules that contain an antigen binding site which specifically binds (immunoreacts with) an antigen, such as a DHY. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind DHY molecules. The term "monoclonal antibody" or "monoclonal antibody composition", as used herein, refers to a population of antibody molecules that contain only one species of an antigen binding site capable of immunoreacting with a particular epitope of DHY. A monoclonal antibody composition thus typically displays a single binding affinity for a particular DHY protein with which it immunoreacts.

Polyclonal anti-DHY antibodies can be prepared as described above by immunizing a suitable subject with a DHY immunogen. The anti-DHY antibody titer in the immunized subject can be monitored over time by standard techniques, such as with an enzyme linked immunosorbent assay (ELISA) using immobilized DHY. If desired, the antibody molecules directed against DHY can be isolated from the mammal (e.g., from the blood) and further purified by well known techniques, such as protein A chromatography to obtain the IgG fraction. At an appropriate time after immunization, e.g., when the anti-DHY antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a DHY immunogen as described above, and the culture supernatants of the resulting hybridoma cells are screened to identify a hybridoma producing a monoclonal antibody that binds DHY.

Any of the many well known protocols used for fusing lymphocytes and immortalized cell lines can be applied for the purpose of generating an anti-DHY monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal.cell lines are mouse myeloma cell lines that are sensitive to culture medium containing hypoxanthine, aminopterin and thymidine ("HAT medium"). Any of a number of myeloma.cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind DHY, e.g., using a standard ELISA assay.

Alternative to preparing monoclonal antibody-secreting hybridomas, a monoclonal anti-DHY antibody can be identified and isolated by screening a recombinant combinatorial immunoglobulin library (e.g., an antibody phage display library) with DHY to thereby isolate immunoglobulin library members that bind DHY. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-DHY antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

An anti-DHY antibody (e.g., monoclonal antibody) can be used to isolate DHY by standard techniques, such as affinity chromatography or immunoprecipitation. An anti-DHY antibody can facilitate the purification of natural DHY from cells and of recombinantly produced DHY expressed in host cells. Moreover, an anti-DHY antibody can be used to detect DHY protein (e.g., in a cellular lysate or cell supernatant) in order to evaluate the abundance and pattern of expression of the DHY protein. Anti-DHY antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding a DHY protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA. segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., DHY proteins, mutant forms of DHY proteins, fusion proteins, and the like).

The recombinant expression vectors of the invention can be designed for expression of DHY proteins in prokaryotic or eukaryotic cells. For example, DHY proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in DHY activity assays, (e.g., direct assays or competitive assays described in detail below), or to generate antibodies specific for DHY proteins, for example. In a preferred embodiment, a DHY fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in E. coli (Wada et al., (1992) *Nucleic Acids Res.* 20:2111–2118). Such alteration of nucleic acid sequences of the invention can be carried out by standard DNA synthesis techniques.

In another embodiment, the DHY expression vector is a yeast expression vector. Examples of vectors for expression in yeast *S. cerevisiae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (In Vitrogen Corp, San Diego, Calif.).

Alternatively, DHY proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to DHY mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a DHY nucleic acid molecule of the invention is introduced, e.g., a DHY nucleic acid molecule within a recombinant expression vector or a DHY nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a DHY protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a DHY protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a DHY protein. Accordingly, the invention further provides methods for producing a DHY protein using the host cells of the invention. In one embodiment, the method comprises culturing the host cell of the invention (into which a recombinant expression vector encoding a DHY protein has been introduced) in a suitable medium such that a DHY protein is produced. In another embodiment, the method further comprises isolating a DHY protein from the medium or the host cell.

The host cells of the invention can also be used to produce non-human transgenic animals. For example, in one embodiment, a host cell of the invention is a fertilized oocyte or an embryonic stem cell into which DHY-coding sequences have been introduced. Such host cells can then be used to create non-human transgenic animals in which exogenous DHY sequences have been introduced into their genome or homologous recombinant animals in which endogenous DHY sequences have been altered. Such animals are useful for studying the function and/or activity of a DHY and for identifying and/or evaluating modulators of DHY activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous DHY gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a DHY-encoding nucleic acid into the male pronuclei of a fertilized oocyte, e.g., by microinjection, retroviral infection, and allowing the oocyte to develop in a pseudopregnant female foster animal. The DHY cDNA sequence of SEQ ID NO:1, SEQ ID NO:4, SEQ ID NO:7, or SEQ ID NO:9 can be introduced as a transgene into the genome of a non-human animal. Alternatively, a nonhuman homologue of human DHY gene, such as a mouse or rat DHY gene, can be used as a transgene. Alternatively, a DHY gene homologue, such as another DHY family member, can be isolated based on hybridization to the DHY cDNA sequences of SEQ ID NO:1 or 3 (described further in subsection I above) and used as a transgene. Intronic sequences and polyadenylation signals can also be included in the transgene to increase the efficiency of expression of the transgene. A tissue-specific regulatory sequence(s) can be operably linked to a DHY transgene to direct expression of a DHY protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a DHY transgene in its genome and/or expression of DHY mRNA in tissues or cells of the animals. A transgenic founder animal can then be used to breed additional animals carrying the transgene. Moreover, transgenic animals carrying a transgene encoding a DHY protein can further be bred to other transgenic animals carrying other transgenes.

To create a homologous recombinant animal, a vector is prepared which contains at least a portion of a DHY gene into which a deletion, addition or substitution has been introduced to thereby alter, e.g., functionally disrupt, the DHY gene. The DHY gene can be a human gene (e.g., the cDNA of SEQ ID NO:3), but more preferably, is a non-human homologue of a human DHY gene (e.g., a cDNA isolated by stringent hybridization with the nucleotide sequence of SEQ ID NO:1). For example, a mouse DHY gene can be used to construct a homologous recombination nucleic acid molecule, e.g., a vector, suitable for altering an endogenous DHY gene in the mouse genome. In a preferred embodiment, the homologous recombination nucleic acid molecule is designed such that, upon homologous recombination, the endogenous DHY gene is functionally disrupted (i.e., no longer encodes a functional protein; also referred to as a "knock out" vector). Alternatively, the homologous recombination nucleic acid molecule can be designed such that, upon homologous recombination, the endogenous DHY gene is mutated or otherwise altered but still encodes functional protein (e.g., the upstream regulatory region can be altered to thereby alter the expression of the endogenous DHY protein). In the homologous recombination nucleic acid molecule, the altered portion of the DHY gene is flanked at its 5' and 3' ends by additional nucleic acid sequence of the DHY gene to allow for homologous recombination to occur between the exogenous DHY gene carried by the homologous recombination nucleic acid molecule and an endogenous DHY gene in a cell, e.g., an embryonic stem cell. The additional flanking DHY nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced DHY gene has homologously recombined with the endogenous DHY gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomzas and Embryonic Stem Cells:A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Currenit Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomlyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The DHY nucleic acid molecules, fragments of DHY proteins, and anti-DHY antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a DHY protein or an anti-DHY antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filteredsolution thereof.

Oral compositions generally include an inert diluentor an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight. preferably about 0.01 to 25 mg/kg body weight, more preferably about 0.1 to 20 mg/kg body weight, and even mole preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic ,gent includes any agent that is detrimental to cells. Examples include taxol, cytochalasin B, gramicidin D, ethidium bromide, emetine, mitomycin, etoposide, tenoposide, vincristine, vinblastine, colchicin, doxoribicin, daunoribicin, dihydroxy anthracin dione mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunortibicin (formerly daunomycin) and doxorubicin), antibiotics (e.g., dactinomycin (formerly actinomycin), bleomycin, mithramycin, and anthramycin (AMC)), and anti-mitotic agents (e.g., vinclistine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"). interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a DHY protein of the invention has one or more of the following activities: 1) modulates metabolism and catabolism of biochemical molecules necessary for energy production or storage (e.g., amino acids, such as serine or threonine), 2) modulates intra- or intercellular signaling, 3) modulates metabolism or catabolism of metabolically important biomolecules, 4) modulates cellular growth and differentiation, 5) modulates cellular proliferation, and 6) modulates production of growth factors and cytokines.

The isolated nucleic acid molecules of the invention can be used, for example, to express DHY protein (e.g., via a recombinant expression vector in a host cell in gene therapy applications), to detect DHY mRNA (e.g., in a biological sample) or a genetic alteration in a DHY gene, and to modulate DHY activity, as described further below. The DHY proteins can be used to treat disorders characterized by insufficient or excessive production of a DHY substrate or production of DHY inhibitors. In addition, the DHY proteins can be used to screen for naturally occurring DHY substrates, to screen for drugs or compounds which modulate DHY activity, as well as to treat disorders characterized by insufficient or excessive production of DHY protein or production of DHY protein forms which have decreased, aberrant or unwanted activity compared to DHY wild type protein (e.g., dehydratase-associated disorders, such as CNS disorders (e.g., Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis, progressive supranuclear palsy, epilepsy, and Jakob-Creutzfieldt disease; autonomic function disorders such as hypertension and sleep disorders, and neuropsychiatric disorders, such as depression, schizophrenia, schizoaffective disorder, korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, and bipolar affective disorder (e.g., severe bipolar affective (mood) disorder (BP-1) and bipolar affective neurological disorders (e.g., migraine and obesity)); cardiac disorders (e.g., arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation, Jervell syndrome, Lange-Nielsen syndrome, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, and arrhythmia); muscular disorders (e.g., paralysis, muscle weakness (e.g., ataxia, myotonia, and myokymia), muscular dystrophy (e.g., Duchenne muscular dystrophy or myotonic dystrophy), spinal muscular atrophy, congenital myopathies, central core disease, rod myopathy, central nuclear myopathy, Lambert-Eaton syndrome, denervation, and infantile spinal muscular atrophy (Werdnig-Hoffman disease); cellular growth, differentiation, or migration disorders (e.g., cancer, e.g., carcinoma, sarcoma, or leukemia; tumor angiogenesis and metastasis; skeletal dysplasia; neuronal deficiencies resulting from impaired neural induction and patterning); hepatic disorders; hematopoletic and/or myeloproliferative disorders; neurological disorders (e.g., Sjogren-Larsson syndrome, disorders in GABA processing or reception). Moreover, the anti-DHY antibodies of the invention can be used to detect and isolate DHY proteins, regulate the bioavailability of DHY proteins, and modulate DHY activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to DHY proteins, have a stimulatory or inhibitory effect on, for example, DHY expression or DHY activity, or have a stimulatory or inhibitory effect on, for example, the expression or activity of DHY substrate.

In one embodiment, the invention provides assays for screening candidate or test compounds which are substrates of a DHY protein or polypeptide or biologically active portion thereof (e.g., amino acids, such as serine or threonine). In another embodiment, the invention provides assays for screening candidate or test compounds which bind to or modulate the activity of a DHY protein or polypeptide or biologically active portion thereof (e.g., cofactor or coenzyme analogs, or inhibitory molecules). The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular, libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) Biotechniques 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a DHY protein or biologically active portion thereof is contacted with a test compound and the ability of the test compound to modulate DHY activity is determined. Determining the ability of the test compound to modulate DHY activity can be accomplished by monitoring, for example, the production of one or more specific metabolites in a cell which expresses DHY (see, e.g., Saada et al. (2000) *Biocheni Biophys. Res. Commut.* 269: 382–386). The cell, for example, can be of mammalian origin, e.g., a neuronal cell or an epithelial cell. The ability of the test compound to modulate DHY binding to a substrate (e.g., an amino acid such as serine or threonine) or to bind to DHY can also be determined. Determining the ability of the test compound to modulate DHY binding to a substrate can be accomplished, for example, by coupling the DHY substrate with a radioisotope or enzymatic label such that binding of the DHY substrate to DHY can be determined by detecting the labeled DHY substrate in a complex. Alternatively, DHY could be coupled with a radioisotope or enzymatic label to monitor the ability of a test compound to modulate DHY binding to a DHY substrate in a complex. Determining the ability of the test compound to bind DHY can be accomplished, for example, by coupling the compound with a radioisotope or enzymatic label such that binding of the compound to DHY can be determined by detecting the labeled DHY compound in a complex. For example, compounds (e.g., DHY substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a DHY substrate) to interact with DHY without the labeling of any of the interactants. For example, a microphysiometer can be used to detect the interaction of a compound with DHY without the labeling of either the compound or the DHY. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and DHY.

In another embodiment, an assay is a cell-based assay comprising contacting a cell expressing a DHY target molecule (e.g., a DHY substrate) with a test compound and determining the ability of the test compound to modulate (e.g., stimulate or inhibit) the activity of the DHY target molecule. Determining the ability of the test compound to modulate the activity of a DHY target molecule can be accomplished, for example, by determining the ability of the DHY protein to bind to or interact with the DHY target molecule.

Determining the ability of the DHY protein, or a biologically active fragment thereof, to bind to or interact with a DHY target molecule can be accomplished by one of the methods described above for determining direct binding. In a preferred embodiment, determining the ability of the DHY protein to bind to or interact with a DHY target molecule can be accomplished by determining the activity of the target molecule. For example, the activity of the target molecule can be determined by detecting induction of a cellular response (i.e., changes in intracellular $K^+$ levels), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a DHY protein or biologically active portion thereof is contacted with a test compound and the ability of the test compound to bind to the DHY protein or biologically :active portion thereof is determined. Preferred biologically active portions of the DHY proteins to be used in assays of the present invention include fragments which participate in interactions with non-DHY molecules, e.g., fragments with high surface probability scores (see, for example, FIG. 2). Binding of the test compound to the DHY protein can be determined either directly or indirectly as described above. In a preferred embodiment, the assay includes contacting: the DHY protein or biologically active portion thereof with a known compound which binds DHY to form an assay mixture, contacting the assay mixture with a test compound, and determining the ability of the test compound to interact with a DHY protein, wherein determining the ability of the test compound to interact with a DHY proteincomprises determining the ability of the test compound to preferentially bind to DHY or biologically active portion thereof as compared to the known compound.

In another embodiment, the assay is a cell-free assay in which a DHY protein or biologically active portion thereof is contacted with a test compound and the ability of the test compound to modulate (e.g., stimulate or inhibit) the activity of the DHY protein or biologically active portion thereof is determined. Determining the ability of the test compound to modulate the activity of a DHY protein can be accomplished, for example, by determining the ability of the DHY protein to bind to a DHY target molecule by one of the methods described above for determining direct binding. Determining the ability of the DHY protein to bind to a DHY target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a DHY protein can be accomplished by determining the ability of the DHY protein to further modulate the activity of a downstream effector of a DHY target molecule. For example, the activity of the effector molecule on an appropriate target can be determined or the binding of the effector to an appropriate target can be determined as previously described.

In yet another embodiment, the cell-free assay involves contacting a DHY protein or biologically active portion thereof with a known compound which binds the DHY protein to form an assay mixture, contacting the assay mixture with a test compound, and determining the ability of the test compound to interact with the DHY protein, wherein determining the ability of the test compound to interact with the DHY protein comprises determining the ability of the DHY protein to preferentially bind to or catalyze the transfer of a hydride moiety to or from the target substrate.

In more than one embodiment of the above assay methods of the present invention, it may be desirable to immobilize either DHY or its target molecule to facilitate separation of complexed from uncomplexed forms of one or both of the proteins, as well as to accommodate automation of the assay. Binding of a test compound to a DHY protein, or interaction of a DHY protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/DHY fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or DHY protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of DHY binding or activity determined using standard techniques.

Other techniques for immobilizing proteins on matrices can also be used in the screening assays of the invention. For example, either a DHY protein or a DHY target molecule can be immobilized utilizing conjugation of biotin and streptavidin. Biotinylated DHY protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with DHY protein or target molecules but which do not interfere with binding of the DHY protein to its target molecule can be derivatized to the wells of the plate, and unbound target or DHY protein trapped in the wells by antibody conjugation. Methods for detecting such complexes, in addition to those described above for the GST-immobilized complexes, include immunodetection of complexes using antibodies reactive with the DHY protein or target molecule, as well as enzyme-linked assays which rely on detecting an enzymatic activity associated with the DHY protein or target molecule.

In another embodiment, modulators of DHY expression are identified in a method wherein a cell is contacted with a candidate compound and the expression of DHY mRNA or protein in the cell is determined. The level of expression of DHY mRNA or protein in the presence of the candidate compound is compared to the level of expression of DHY mRNA or protein in the absence of the candidate compound. The candidate compound can then be identified as a modulator of DHY expression based on this comparison. For example, when expression of DHY mRNA or protein is greater (statistically significantly greater) in the presence of the candidate compound than in its absence, the candidate compound is identified as a stimulator of DHY mRNA or protein expression. Alternatively, when expression of DHY mRNA or protein is less (statistically significantly less) in the presence of the candidate compound than in its absence, the candidate compound is identified as an inhibitor of DHY mRNA or protein expression. The level of DHY mRNA or protein expression in the cells can be determined by methods described herein for detecting DHY mRNA or protein.

In yet another aspect of the invention, the DHY proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with DHY ("DHY-binding proteins" or "DHY-6-bp") and are involved in DHY activity. Such DHY-binding proteins are also likely to be involved in the propagation of signals by the DHY proteins or DHY targets as, for example, downstream elements of a DHY-mediated signaling pathway. Alternatively, such DRY-binding proteins are likely to be DHY inhibitors.

The two-hybrid system is based on the modular nature of most transcription factors, which consist of separable DNA-binding and activation domains. Briefly, the assay utilizes two different DNA constructs. In one construct, the gene that codes for a DHY protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a DHY-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the DHY protein.

In another aspect, the invention pertains to a combination of two or more of the assays described herein. For example, a modulating agent can be identified using a cell-based or a cell free assay, and the ability of the agent to modulate the activity of a DHY protein can be confirmed in vivo, e.g., in an animal such as an animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., a DHY modulating agent, an antisense DHY nucleic acid molecule, a DHY-specific antibody, or a DHY-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the DHY nucleotide sequences, described herein, can be used to map the location of the DHY genes on a chromosome. The mapping of the DHY sequences to chromosomes is an important first step in correlating these sequences with genes associated with disease.

Briefly, DHY genes can be mapped to chromosomes by preparing PCR primers (preferably 15–25 bp in length) from the DHY nucleotide sequences. Computer analysis of the DHY sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the DHY sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the DHY nucleotide sequences to design oligonucleotide primers, sublocalization can be achieved with panels of fragments from specific chromosomes. Other mapping strategies which can similarly be used to map a DHY sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical rposition of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the DHY gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The DHY sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the DHY nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The DHY nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as that in SEQ ID NO:3, are used, a more appropriate number of primers for positive individual identification would be 500–2,000.

If a panel of reagents from DHY nucleotide sequences describedherein is used to generate a unique identification database for an individual, those same reagents can later be used to identify tissue from that individual. Using the unique identification database, positive identification of the individual, living or dead, can be made from extremely small tissue samples.

3. Use of DHY Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the DHY nucleotide sequences or portions thereof, e.g., fragments derived from the noncoding regions of SEQ ID NO:1 having a length of at least 20 bases, preferably at least 30 bases.

The DHY nucleotide sequences described herein can further be used to provide polynucleotide reagents, e.g., labeled or labelable probes which can be used in, for example, an in situ hybridization technique, to identify a specific tissue, e.g., thymus or brain tissue. This can be very useful in cases where a forensic pathologist is presented with a tissue of unknown origin. Panels of such DHY probes can be used to identify tissue by species and/or by organ type. In a similar fashion, these reagents, e.g., DHY primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining DHY protein and/or nucleic acid expression as well as DHY activity, in the context of a biological sample (e.g., blood, serum, cells, tissue) to thereby determine whether an individual is afflicted with a disease or disorder, or is at risk of developing a disorder, associated with aberrant or unwanted DHY expression or activity. The invention also provides for prognostic (or predictive) assays for determining whether an individual is at risk of developing a disorder associated with DHY protein, nucleic acid expression or activity. For example, mutations in a DHY gene can be assayed in a biological sample. Such assays can be used for prognostic or predictive purpose to thereby phophylactically treat an individual prior to the onset of a disorder characterized by or associated with DHY protein, nucleic acid expression or activity.

Another aspect of the invention pertains to monitoring the influence of agents (e.g., drugs, compounds) on the expression or activity of DHY in clinical trials.

These and other agents are described in further detail in the following sections.

1. Diagnostic Assays

An exemplary method for detecting the presence or absence of DHY protein or nucleic acid in a biological sample involves obtaining a biological sample from a test subject and contacting the biological sample with a compound or an agent capable of detecting DHY protein or nucleic acid (e.g., mRNA, or genomic DNA) that encodes DHY protein such that the presence of DHY protein or nucleic acid is detected in the biological sample. A preferred agent for detecting DHY mRNA or genomic DNA is a labeled nucleic acid probe capable of hybridizing to DHY mRNA or genomic DNA. The nucleic acid probe can be, for example, the DHY nucleic acid set forth in SEQ ID NO:1 or 3, or a portion thereof, such as an oligonucleotide of at least 15, 30, 50, 100, 250 or 500 nucleotides in length and sufficient to specifically hybridize under stringent conditions to DHY mRNA or genomic DNA. Other suitable probes for use in the diagnostic assays of the invention are described herein.

A preferred agent for detecting DHY protein is an antibody capable of binding to DHY protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibodyusing a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect DHY mRNA, protein, or genomic DNA in a biological sample in vitro as well as in vivo. For example, in vitro techniques for detection of DHY mRNA include Northern hybridizations and in situ hybridizations. In vitro techniques for detection of DHY protein include enzyme linked immunosorbent assays (ELISAs), Western blots, immunoprecipitations and immunofluorescence. In vitro techniques for detection of DHY genomic DNA include Southern hybridizations. Furthermore, in vivo techniques for detection of DHY protein include introducing into a subject a labeled anti-DHY antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting DHY protein, mRNA, or genomic DNA, such that the presence of DHY protein, mRNA or genomic DNA is detected in the biological sample, and comparing the presence of DHY protein, mRNA or genomic DNA in the control sample with the presence of DHY protein, mRNA or genomic DNA in the test sample.

The invention also encompasses kits for detecting the presence of DHY in a biological sample. For example, the kit can comprise a labeled compound or agent capable of detecting DHY protein or mRNA in a biological sample; means for determining the amount of DHY in the sample; and means for comparing the amount of DHY in the sample with a standard. The compound or agent can be packaged in a suitable container. The kit can further comprise instructions for using the kit to detect DHY protein or nucleic acid.

2. Prognostic Assays

The diagnostic methods described herein can furthermore be utilized to identify subjects having or at risk of developing a disease or disorder associated with aberrant or unwanted DHY expression or activity. As used herein, the term "aberrant" includes a DHY expression or activity which deviates from the wild type DHY expression or activity. Aberrant expression or activity includes increased or decreased expression or activity, as well as expression or activity which does not follow the wild type developmental pattern of expression or the subcellular pattern of expression. For example, aberrant DHY expression or activity is intended to include the cases in which a mutation in the DHY gene causes the DHY gene to be under-expressed or over-expressed and situations in which such mutations result in a non-functional DHY protein or a protein which does not function in a wild-type fashion, e.g., a protein which does not interact with a DHY substrate, or one which interacts with a non-DHY substrate. As used herein, the term "unwanted" includes an unwanted phenomenon involved in a biological response such as cellular proliferation. For example, the term unwanted includes a DHY expression or activity which is undesirable in a subject.

The assays described herein, such as the preceding diagnostic assays or the following assays, can be utilized to identify a subject having or at risk of developing a disorder associated with a misregulation in DHY protein activity or nucleic acid expression, such as a CNS disorder (e.g., a cognitive or neurodegenerative disorder), a cellular proliferation, growth, differentiation, or migration disorder, a cardiovascular disorder, or a musculoskeletal disorder. Alternatively, the prognostic assays can be utilized to identify a subject having or at risk for developing a disorder associated with a misregulation in DHY protein activity or nucleic acid expression, such as a CNS disorder, a cellular proliferation, growth, differentiation, or migration disorder, a musculoskeletal disorder, or a cardiovascular disorder. Thus, the present invention provides a method or identifying a disease or disorder associated with aberrant or unwanted DHY expression or activity in which a test sample is obtained from a subject and DHY protein or nucleic acid (e.g., mRNA or genomic DNA) is detected, wherein the presence of DHY protein or nucleic acid is diagnostic for a subject having or at risk of developing a disease or disorder associated with aberrant or unwanted DHY expression or activity. As used herein, a "test sample" refers to a biological sample obtained from a subject of interest. For example, a test sample can be a biological fluid (e.g., cerebrospinal fluid orserum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted DHY expression or activity. For example, such methods can be used to determine whether a subject can be effectively treated with an agent for a CNS disorder, a muscular disorder, or a cellular proliferation, growth, differentiation, or migration disorder. Thus, the present invention provides methods for determining whether a subject can be effectively treated with an agent for a disorder associated with aberrant or unwanted DHY expression or activity in which a test sample is obtained and DHY protein or nucleic acid expression or activity is detected (e.g., wherein the abundance of DHY protein or nucleic acid expression or activity is diagnostic for a subject that can be administered the agent to treat a disorder associated with aberrant or unwanted DHY expression or activity).

The methods of the invention can also be used to detect genetic alterations in a DHY gene, thereby determining if a subject with the altered gene is at risk for a disorder characterized by misregulation in DHY protein activity or nucleic acid expression, such as a CNS disorder, a musculoskeletal disorder, a cellular proliferation, growth, differentiation, or migration disorder, or a cardiovascular disorder. In preferred embodiments, the methods include detecting, in a sample of cells from the subject, the presence or absence of a genetic alteration characterized by at least one of an alteration affecting the integrity of a gene encoding a DHY-protein, or the mis-expression of the DHY gene. For example, such genetic alterations can be detected by ascertaining the existence of at least one of 1) a deletion of one or more nucleotides from a DHY gene; 2) an addition of one or more nucleotides to a DHY gene; 3) a substitution of one or more nucleotides of a DHY gene, 4) a chromosomal rearrangement of a DHY gene; 5) an alteration in the level of a messenger RNA transcript of a DHY gene, 6) aberrant modification of a DHY gene, such as of the methylation pattern of the genomic DNA, 7) the presence of a non-wild type splicing pattern of a messenger RNA transcript of a DHY gene, 8) a non-wild type level of a DHY-protein, 9) allelic loss of a DHY gene, and 10) inappropriate post-translational modification of a DHY-protein. As described herein, there are a large number of assays known in the art which can be used for detecting alterations in a DHY gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in a DHY gene (see Abravaya et al. (1995) *Nucleic Acids Res.* 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a DHY gene under conditions such that hybridization and amplification of the DHY gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a DHY gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in DHY can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in DHY can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the DHY gene and detect mutations by comparing the sequence of the sample DHY with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the DHY gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type DHY sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in DHY cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a DHY sequence, e.g., a wild-type DHY sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in DHY genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat. Res.* 285:125–144; and Hayashi (1992) *Genet. Anal. Tech. Appl.* 9:73–79). Single-stranded DNA fragments of sample and control DHY nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally an d then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991)

*Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The method s described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a DHY gene.

Furthermore, any cell type or tissue in which DHY is expressed may be utilized in the prognostic assays described herein.

3. Monitoring of Effects During, Clinical Trials

Monitoring the influence of agents (e.g., drugs) on the expression or activity of a DHY protein (e.g., the modulation of cell proliferation and/or migration) can be applied not only in basic drug screening, but also in clinical trials. For example, the effectiveness of an agent determined by a screening assay as described herein to increase DHY gene expression, protein levels, or upregulate DHY activity, can be monitored in clinical trials of subjects exhibiting decreased DHY gene expression, protein levels, or down-regulated DHY activity. Alternatively, the effectiveness of an agent determined by a screening assay to decrease DHY gene expression, protein levels, or downregulate DHY activity, can be monitored in clinical trials of subjects exhibiting increased DHY gene expression, protein levels, or upregulated DHY activity. In such clinical trials, the expression or activity of a DHY gene, and preferably, other genes that have been implicated in, for example, a DHY-associated disorder can be used as a "read out" or markers of the phenotype of a particular cell.

For example, and not by way of limitation, genes, including DHY, that are modulated in cells by treatment with an agent (e.g., compound, drug or small molecule) which modulates DHY activity (e.g., identified in a screening assay as described herein) can be identified. Thus, to study the effect of agents on DHY-associated disorders (e.g., disorders characterized by deregulated cell proliferation and/or migration), for example, in a clinical trial, cells can be isolated and RNA prepared and analyzed for the levels of expression of DHY and other genes implicated in the DHY-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of DHY or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a DHY protein, mRNA, or genomic DNA in the preadministration sample; (iii) obtaining one or more post-administration samples from the subject; (iv) detecting the level of expression or activity of the DHY protein, mRNA, or genomic DNA in the post-administration samples; (v) comparing the level of expression or activity of the DHY protein, mRNA, or genomic DNA in the pre-administration sample with the DHY protein, mRNA, or genomic DNA in the post -administration sample or samples; and (vi) altering the administration of the agent to the subject accordingly. For example, increased administration of the agent may be desirable to increase the expression or activity of DHY to higher levels than detected, i.e., to increase the effectiveness of the agent. Alternatively, decreased administration of the agent may be desirable to decrease expression or activity of DHY to lower levels than detected, i.e. to decrease the effectiveness of the agent. According to such an embodiment, DHY expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant or unwanted DHY expression or activity, e.g., a dehydratase-associated disorder such as a CNS disorder; a cellular proliferation, growth, differentiation, or migration disorder; a, musculoskeletal disorder; or a cardiovascular disorder. "Treatment", as used herein, is defined as the application or administration of a therapeutic agent to a patient, or application or administration of a therapeutic agent to an isolated tissue or cell line from a patient, who has a disease or disorder, a symptom of disease or disorder or a predisposition toward a disease or disorder, with the purpose of curing, healing, alleviating, relieving, altering, remedying, ameliorating, improving or affecting the disease or disorder, the symptoms of disease or disorder or the predisposition toward a disease or disorder. A therapeutic agent includes, but is not limited to, small molecules, peptides, antibodies, ribozymes and antisense oligonucleotides. With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the DHY molecules of the present invention or DHY modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted DHY expression or activity, by administering to the subject a DHY or an agent which modulates DHY expression or at least one DHY activity. Subjects at risk for a disease which is caused or contributed to by aberrant or unwanted DHY expression or activity can be identified by, for example, any or a combination of diagnostic or prognostic assays as described herein. Administration of a prophylactic agent can occur prior to the manifestation of symptoms characteristic of the DHY aberrancy, such that a disease or disorder is prevented or, alternatively, delayed in its progression. Depending on the type of DHY aberrancy, for example, a DHY, DHY agonist or DHY antagonist agent can be used for treating the subject. The appropriate agent can be determined based on screening assays described herein.

2. Therapeutic Methods

Another aspect of the invention pertains to methods of modulating DHY expression or activity for therapeutic purposes. Accordingly, in an exemplary embodiment, the modulatory method of the invention involves contacting a cell with a DHY or agent that modulates one or more of the activities of DHY protein activity associated with the cell. An agent that modulates DHY protein activity can be an agent as described herein, such as a nucleic acid or a protein, a naturally-occurring target molecule of a DHY protein (e.g., a DHY substrate), a DHY antibody, a DHY agonist or antagonist, a peptidomimetic of a DHY agonist or antagonist, or other small molecule. In one embodiment, the agent stimulates one or more DHY activities. Examples of such stimulatory agents include active DHY protein and a nucleic acid molecule encoding DHY that has been introduced into the cell. In another embodiment, the agent inhibits one or more DHY activities. Examples of such inhibitory agents include antisense DHY nucleic acid molecules, anti-DHY antibodies, and DHY inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a DHY protein or nucleic acid molecule. In one embodiment, the method involves administering an agent (e.g., an agent identified by a screening assay described herein), or combination of agents that modulates (e.g., upregulates or downregulates) DHY expression or activity. In another embodiment, the method involves administering a DHY protein or nucleic acid molecule as therapy to compensate for reduced, aberrant, or unwanted DHY expression or activity.

Stimulation of DHY activity is desirable in situations in which DHY is abnormally downregulated and/or in which increased DHY activity is likely to have a beneficial effect. Likewise, inhibition of DHY activity is desirable in situations in which DHY is abnormally upregulated and/or in which decreased DHY activity is likely to have a beneficial effect.

3. Pharmacogenomics

The DHY molecules of the present invention, as well as agents, or modulators which have a stimulatory or inhibitory effect on DHY activity (e.g., DHY gene expression) as identified by a screening assay described herein can be administered to individuals to treat (prophylactically or therapeutically) DHY-associated disorders (e.g., proliferative disorders, CNS disorders, cardiac disorders, metabolic disorders, or muscular disorders) associated with aberrant or unwanted DHY activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a DHY molecule or DHY modulator as well as tailoring the dosage and/or therapeutic regimen of treatment with a DHY molecule or DHY modulator.

Pharmacogenomics deals with clinically significant hereditary variations in the response to drugs due to altered drug disposition and abnormal action in affected persons. See, for example, Eichelbaum, M. et al. (1996) Clin. Exp-.Pharmacol. Physiol. 23(10–11): 983–985 and Linder, M. W. et al. (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million-known single nucleotide polymorphisms (SNPs) in the human genome. As used herein, a"SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a DHY protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a DHY molecule or DHY modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a DHY molecule or DHY modulator, such as a modulator identified by one of the exemplary screening assays described herein.

VI. Electronic Apparatus Readable Media and Arrays

Electronic apparatus readable media comprising DHY sequence information is also provided. As used herein, "DHY sequence information" refers to any nucleotide and/or amino acid sequence information particular to the DHY molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said DHY sequence information includes detection of the presence or absence of a sequence (e.g., detection of expression of a sequence, fragment, polymorphism, etc.), determination of the level of a sequence (e.g., detection of a level of expression, for example, a quantative detection), detection of a reactivity to a sequence (e.g., detection of protein expression and/or levels, for example, using a sequence-specific antibody), and the like. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon DHY sequence information of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the DHY sequence information.

A variety of software programs and formats can be used to store the sequence information on the electronic apparatus readable medium. For example, the sequence information can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon the DHY sequence information.

By providing DHY sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a DHY-associated disease or disorder or a pre-disposition to a DHY-associated disease or disorder, wherein the method comprises the steps of determining DHY sequence information associated with the subject and based on the DHY sequence information, determining whether the subject has a DHY-associated disease or disorder or a pre-disposition to a DHY-associated disease or disorder and/or recommending a particular treatment for the disease, disorder or pre-disease condition.

The present invention further provides in an electronic system and/or in a network, a method for determining whether a subject has a DHY-associated disease or disorder or a pre-disposition to a disease associated with a DHY wherein the method comprises the steps of determining DHY sequence information associated with the subject, and based on the DHY sequence information, determining whether the subject has a DHY-associated disease or disorder or a pre-disposition to a DHY-associated disease or disorder, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a DHY-associated disease or disorder or a pre-disposition to a DHY associated disease or disorder associated with DHY, said method comprising the steps of receiving DHY sequence information from the subject and/or information related thereto, receiving phenotypic information associated with the subject, acquiring information from the network corresponding to DHY and/or a DHY-associated disease or disorder, and based on one or more of the phenotypic information, the DHY information (e.g., sequence information and/or information related thereto), and the acquired information, determining whether the subject has a DHY-associated disease or disorder or a pre-disposition to a DHY-associated disease or disorder (e.g., CNS disorder; a cellular proliferation, growth, differentiation, or migration disorder; a musculoskeletal disorder; or a cardiovascular disorder). The method may further comprise the step of recommending a particular treatment for the disease, disorder or pre-disease condition.

The present invention also provides a business method for determining whether a subject has a DHY-associated disease or disorder or a pre-disposition to a DHY-associated disease or disorder, said method comprising the steps of receiving information related to DHY (e.g., sequence information and/or information related thereto), receiving phenotypic information associated with the subject, acquiring information from the network related to DHY and/or related to a DHY-associated disease or disorder, and based on one or more of the phenotypic information, the DHY information, and the acquired information, determining whether the subject has a DHY-associated disease or disorder or a pre-disposition to a DHY-associated disease or disorder. The method may further comprise the step of recommending a particular treatment for the disease, disorder or pre-disease condition.

The invention also includes an array comprising a DHY sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be DHY. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a DHY-associated disease or disorder, progression of DHY-associated disease or disorder, and processes, such a cellular transformation associated with the DHY-associated disease or disorder.

The array is also useful for ascertaining the effect of the expression of a gene on the expression of other genes in the same cell or in different cells (e.g., ascertaining the effect of DHY expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including DHY) that could serve as a molecular target for diagnosis or therapeutic intervention.

This invention is further illustrated by the following examples which should not be construed as limiting. The contents of all references, patents and published patent applications cited throughout this application, as well as the Figures, are incorporated herein by reference.

EXAMPLES

Example 1

Identification and Characterization of Human DHY cDNA

In this example, the identification and characterization of the gene encoding human DHY (clone Fbh26335) is described.

Isolation of the DHY cDNA

The invention is based, at least in part, on the discovery of a human gene encoding a novel protein, referred to herein as DHY. The entire sequence of human clone fbh26335 was determined and found to contain an open reading frame termed human "DHY", set forth in FIGS. 1A–B. The amino acid sequence of the human DHY expression product is set forth in FIGS. 1A–B. The DHY protein sequence set forth in SEQ ID NO:2 comprises about 329 amino acids and is shown in FIGS. 1A–B. The coding region (open reading frame) of SEQ ID NO:1, is set forth as SEQ ID NO:3.

Analysis of the Human DHY Molecule

The amino acid sequence of human DHY was analyzed using the program PSORT (http://www.psort.nibb.ac.jp) to predict the localization of the protein within the cell. This program assesses the presence of different targeting and localization amino acid sequences within the query sequence. The results of the analysis show that human DHY (SEQ ID NO:2) may be localized to the cytoplasm, to the mitochondrion, to golgi, to the endoplasmic reticulum, extracellular to the cell or to the cell wall, to vacuoles, to the nucleus, or to secretory vesicles.

A search of the amino acid sequence of DHY was performed against the Memsat database (FIG. 3). This search resulted in the identification of four transmembrane domains in the amino acid sequence of human DHY (SEQ ID NO:2) at about residues 67–83, 167–187, 270–288, and 295–311.

A search of the amino acid sequence of DHY was also performed against the ProSite database (FIG. 4). This search resulted in the identification of a "serine/threconine dehydrate pyridoxal-phosphate attachment site" in the amino acid sequence of DHY (SEQ ID NO:2) at about residues 39–52 (FIG. 4).

A search of the amino acid sequence of DHY was also performed against the HMM database (FIG. 5). This search resulted in the identification of a "serine/thieonine dehydratase domain" in the amino acid sequence of DHY (SEQ ID NO:2) at about residues 11–311 (score=229.5).

A search of the amino acid sequence of DHY was also performed against the ProDom database (FIG. 6). This search resulted in the identification of a "pyridoxal phosphate-dependent lyase synthase domain" in the amino acid sequence of human DHY (SEQ ID NO:2) at about residues 18–282 (score=88).

Tissue Distribution of DHY mRNA

This example describes the tissue distribution of DHY mRNA, as determined by Northern analysis, by Polymerase Chain Reaction (PCR) on cDNA libraries using oligonucleotide primers based on the human DHY sequence, or by in situ analysis.

Northern blot hybridizations with the various RNA samples are performed under standard conditions and washed under stringent conditions, i.e., 0.2×SSC at 65° C. The DNA probe is radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) are probed in ExpressHyb hybridization solution (Clontech) and washed at high stringency according to manufacturer's recommendations.

For in situ analysis, various tissues, e.g. tissues obtained from brain, are first frozen on dry ice. Ten-micrometer-thick sections of the tissues are postfixed with 4% formaldehyde in DEPC treated 1× phosphate- buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections are rinsed in DEPC 2×SSC (1×SSC is 0.15M NaCl plus 0.015M sodium citrate). Tissue is then dehydrated through a series of ethanol washes, incubated in 100% chloroform for 5 minutes, and then rinsed in 100% ethanol for 1 minute and 95% ethanol for 1 minute and allowed to air dry.

Hybridizations are performed with $^{35}$S-radiolabeled (5×10$^7$ cpm/ml) cRNA probes. Probes are incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1×Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides are washed with 2×SSC. Sections are then sequentially incubated at 37° C. in TNE (a solution containing 10 mM Tris-HCl (pH 7.6), 500 mM NaCl, and 1 mM EDTA), for 10 minutes, in TNE with 10 □g of RNase A per ml for 30 minutes, and finally in TNE for 10 minutes. Slides are then rinsed with 2×SSC at room temperature, washed with 2×SSC at 50° C. for 1 hour, washed with 0.2×SSC at 55° C. for 1 hour, and 0.2×SSC at 60° C. for 1 hour. Sections are then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

Tissue Distribution of human DHY mRNA using Taqman™ analysis

This example describes the tissue distribution of human DHY mRNA in a variety of cells and tissues, as determined using the TaqMan™ procedure. The Taqman™ procedure is a quantitative, reverse transcription PCR-based approach for detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest, e.g., various human normal and cancer samples, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxyfluorescein), TET (6-carboxy-4,7, 2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control gene confirms efficient removal of genomic DNA contamination.

Highest expression of DHY mRNA was detected in HMVECL, U937/A10P10, bronchial epithelium, astrocytes, primary osteoblasts, keratinocytes, bronchial epithelium mix (BEA8-2B), congestive heart failure (CHF) heart tissue, the pituitary gland, fetal kidney tissue, fetal liver tissue, mesangial, T24Ctl, T24 (treated), adrenal gland tissue, Burkitt's Lymphoma tissue, mammary epithelium, WT LNCap+ casodex, A549 IL-1, SCC25 CDDP-tongue squamous cell carcinoma tissue, testes, K563 (red blood cell line), A459 control (random-primed), liver tissue, prostate tissue, normal colon tissue, HMC-1 (mast cell line), normal megakarocytes, colon to liver metastasis (CHT128), colon to liver metastasis (CHT133), normal breast tissue, PTH osteo, lung squamous cell carcinoma tissue PIT299, and d8 dendritic cells.

Lesser expression was also detected in HUVECL, HL60/S, prostate epithelium, coronary smooth muscle cells, fetal lung tissue, fetal thymus tissue, congestive heart failure (CHF) heart tissue, prostate smooth muscle tissue, thyroid tissue, LPS 24 hour osteoblasts, uterine smooth muscle tissue (treated), bronchial smooth muscle tissue, umbilical smooth muscle tissue (treated), A2780 WT, fetal liver tissue, fetal skin, fetal adrenal gland tissue, midterm placental tissue, lung carcinoma tissue, embryonic keritinocytes, testes, skin, adipose, placental tissue (random-primed), kidney tissue (random-primed), HPK (random primed), salivary gland, heart tissue, the thymus, stomach tissue, spleen tissue, small intestine tissue, normal breast epithelia, normal ovarian epithelia, colon carcinoma tissue, ovarian ascites, serum starved embryonic lung tissue, lung squamous cell carcinoma tissue, brain subcortical white matter, normal prostate tissue (ziplox), HUVEC L (umbilical endothelium).

No expression was detected in U937/A10p50, CaCo, Hela cells, HL60/Adr, fetal brain tissue, melanocytes, cerebellum, aortic endothelial cells, prostate fibroblast tissue, mammary gland tissue, natural killer cells, LPS 1 hr. osteoblasts, LPS 6 hr. osteoblasts, WT LNCap+ testosterone, A2780ADR, fetal spleen tissue, the esophagus, p65 con +/+, p65 IL-1 +/+, pulmonary artery smooth muscle tissue, erythroleukemia cells, SCC25 WT-tongue squamous cell carcinoma tissue, fetal hypothalamus, T cells (CD3 treated), T cells (CD3 IL-4/IL-10 treated), T cells (CD3 IFNg/TFNa treated), trachea tissue, ME180 IL-1 cervical carcinoma tissue, ME 180 control, MCP-1 mast cell line, HPKII, lung tissue (random primed), heart tissue (random primed), fetal brain tissue (random primed), testes (random primed), RAJI (Burkitt's lymphoma B cell), ST 486 (lymphoma B cell), HL60 (acute promyelocytic leukemia), umbilical cord smooth muscle tissue (treated, random primed), uterine smooth muscle (treated, random primed), mammary gland tissue (random primed), small intestine tissue (random primed), fetal liver tissue (random primed), skeletal liver tissue (random primed), stomach tissue (random primed), spleen tissue (random primed), liver tissue (random primed), brain tissue (random primed), uterine tissue, uterine tissue (random primed), thymus tissue (random primed), 9 week fetus, lung tissue, skeletal muscle, retinal pigmentosa epithelial tissue, retinal tissue, bone marrow, Th-1 induced T cell, Th-2 induced T cell, colon carcinoma tissue (NDR 109), colon carcinoma tissue (NDR82), fetal dorsal spinal cord tissue, lung adenocarcinoma tissue (PIT245), megakaryocytes, BMCD34+, IBD colon tissue, cervical cancer tissue, spinal cord, dorsal root ganglia, and ovarian epithelium tumor tissue.

Example 2

Expression of Recombinant DHY Protein in Bacterial Cells

In this example, DHY is expressed as a recombinant glutathione-S-transferase (GST) fusion polypeptide in *E. coli* and the fusion polypeptide is isolated and characterized. Specifically, DHY is fused to GST and this fusion polypeptide is expressed in *E. coli*, e.g., strain PEB199. Expression of the GST-DHY fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant DHY Protein in COS Cells

To express the DHY gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire DHY protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the DHY DNA sequence is amplified by PCR using two primers. The 5' primer contains the restriction site of interest followed by approximately twenty nucleotides of the DHY coding sequence starting from the initiation codon; the 3' end sequence contains complementary sequences to the other restriction site of interest, a translation stop codon, the HA tag or FLAG tag and the last 20 nucleotides of the DHY coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the DHY gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the DHY-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the DHY polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA-specific monoclonal antibody. Precipitated polypeptides are then analyzed by SDS-PAGE.

Alternatively, DNA containing the DHY coding sequence is cloned directly into the polylinker of the pCDNA/Amp vector using the appropriate restriction sites. The resulting plasmid is transfected into COS cells in the manner described above, and the expression of the DHY polypeptide is detected by radiolabelling and immunoprecipitation using a DHY specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. An isolated nucleic acid molecule comprising the nucleotide sequence set forth in SEQ ID NO:1, or a complement thereof.

2. An isolated nucleic acid molecule comprising the nucleotide sequence set forth in SEQ ID NO:3, or a complement thereof.

3. An isolated nucleic acid molecule consisting of the nucleotide sequence set forth in SEQ ID NO:1, or a complement thereof.

4. An isolated nucleic acid molecule consisting of the nucleotide sequence set forth in SEQ ID NO:3, or a complement thereof.

5. An isolated nucleic acid molecule which encodes a polypeptide comprising the amino acid sequence set forth in SEQ ID NO:2, or a complement thereof.

6. An isolated nucleic acid molecule which encodes a polypeptide consisting of the amino acid sequence set forth in SEQ ID NO:2, or a complement thereof.

7. An isolated nucleic acid molecule comprising a nucleotide sequence, the entire sequence of which is at least 90% identical to the entire nucleotide sequence of SEQ ID NO:1, or a complement thereof.

8. An isolated nucleic acid molecule consisting of a nucleotide sequence, the entire sequence of which is at least 90% identical to the entire nucleotide sequence of SEQ ID NO:1, or a complement thereof.

9. An isolated nucleic acid molecule which encodes a protein comprising an amino acid sequence at least 99% identical to the entire amino acid sequence of SEQ ID NO:2.

10. An isolated nucleic acid molecule which encodes a protein consisting of an amino acid sequence at least 99% identical to the entire amino acid sequence of SEQ ID NO:2.

11. An isolated nucleic acid molecule which encodes a polypeptide comprising an amino acid sequence at least 99% identical to the entire amino acid sequence of SEQ ID NO:2, wherein said polypeptide is capable of modulating cellular growth and differentiation.

12. An isolated nucleic acid molecule comprising a nucleotide sequence, the entire sequence of which is at least 90% identical to the entire nucleotide sequence of SEQ ID NO:3, or a complement thereof.

13. An isolated nucleic acid molecule consisting of a nucleotide sequence, the entire sequence of which is at least 90% identical to the entire nucleotide sequence of SEQ ID NO:3, or a complement thereof.

14. A method for detecting the presence of a nucleic acid molecule of any one of claims 1–13 in a sample comprising:
   a) contacting the sample with a nucleic acid probe or primer which selectively hybridizes to the nucleic acid molecule; and
   b) determining whether the nucleic acid probe or primer binds to a nucleic acid molecule in the sample to thereby detect the presence of a nucleic acid molecule of any one of claims 1–13 in the sample.

15. The method of claim 14, wherein the sample comprises mRNA molecules and is contacted with a nucleic acid probe.

16. An isolated nucleic acid molecule comprising the nucleic acid molecule of any one of claims 1–13, and a nucleotide sequence encoding a heterologous polypeptide.

17. A vector, comprising the nucleic acid molecule of any one of claims 1–13.

18. The vector of claim 17, which is an expression vector.

19. A host cell transfected with the expression vector of claim 18.

20. A method of producing a polypeptide comprising culturing the host cell of claim 19 under conditions in which the nucleic acid molecule is expressed, thereby expressing the polypeptide.

21. A kit comprising the nucleic acid molecule of any one of claims 1–13 and instructions for use.

22. A composition comprising the nucleic acid molecule of any one of claims 1–13.

23. The method of claim 14, wherein said probe or primer is detectably labeled.

24. The method of claim 14, wherein said detecting is by in situ hybridization.

25. The method of claim 14, wherein said sample comprises a cell.

26. The method of claim 14, wherein said probe or primer comprises the complement of SEQ ID NO:1 or SEQ ID NO:3, or a fragment thereof.

* * * * *

SEQUENCE LISTING

<160> NUMBER OF SEQ ID NOS: 3

<210> SEQ ID NO 1
<211> LENGTH: 1327
<212> TYPE: DNA
<213> ORGANISM: Homo sapien
<220> FEATURE:
<221> NAME/KEY: CDS
<222> LOCATION: (107)...(1096)

<400> SEQUENCE: 1

```
cacgcgtccg ggaaagagct ggttccctgg caggctggag ggcaggagct ggggccacgc      60
tggtctggga tagttgggca gggaggctgt ctacctggtc tccaga atg gac ggc        115
                                                    Met Asp Gly
                                                      1 cct gtg gca gag cat gcc aag cag gag ccc ttt cac gtg gtc aca cct      163
Pro Val Ala Glu His Ala Lys Gln Glu Pro Phe His Val Val Thr Pro
      5                  10                  15 ctg ttg gag agc tgg gcg ctg tcc cag gtg gcg ggc atg cct gtc ttc      211
Leu Leu Glu Ser Trp Ala Leu Ser Gln Val Ala Gly Met Pro Val Phe
 20                  25                  30                  35 ctc aag tgt gag aat gtg cag ccc agc ggc tcc ttc aag att cgg ggc      259
Leu Lys Cys Glu Asn Val Gln Pro Ser Gly Ser Phe Lys Ile Arg Gly
              40                  45                  50 att ggg cat ttc tgc cag gag atg gcc aag aag gga tgc aga cac ctg      307
Ile Gly His Phe Cys Gln Glu Met Ala Lys Lys Gly Cys Arg His Leu
          55                  60                  65 gtg tgc tcc tca ggg ggt aat gcg ggc atc gct gct gcc tat gct gct      355
Val Cys Ser Ser Gly Gly Asn Ala Gly Ile Ala Ala Ala Tyr Ala Ala
      70                  75                  80 agg aag ctg ggc att cct gcc acc atc gtg ctc ccc gag agc acc tcc      403
Arg Lys Leu Gly Ile Pro Ala Thr Ile Val Leu Pro Glu Ser Thr Ser
 85                  90                  95 ctg cag gtg gtg cag agg ctg cag gcg gag ggg gcc gag gtt cag ctg      451
Leu Gln Val Val Gln Arg Leu Gln Ala Glu Gly Ala Glu Val Gln Leu
100                 105                 110                 115 act gga aag gtc tgg gac gag gcc aat ctg agg gcg caa gag ttg gcc      499
Thr Gly Lys Val Trp Asp Glu Ala Asn Leu Arg Ala Gln Glu Leu Ala
                120                 125                 130 aag agg gac ggc tgg gag aat gtc ccc ccg ttt gac cac ccc cta ata      547
Lys Arg Asp Gly Trp Glu Asn Val Pro Pro Phe Asp His Pro Leu Ile
            135                 140                 145 tgg aaa ggc cac gcc agc ctg gtg cag gag ctg aaa gca gtg ctg agg      595
Trp Lys Gly His Ala Ser Leu Val Gln Glu Leu Lys Ala Val Leu Arg
        150                 155                 160 acc cca cca ggt gcc ctg gtg ctg gca gtt ggg ggt ggg ggt ctc ctg      643
Thr Pro Pro Gly Ala Leu Val Leu Ala Val Gly Gly Gly Gly Leu Leu
    165                 170                 175 gcc ggg gtg gtg gct ggc ctg ctg gag gtg ggc tgg cag cat gta ccc      691
Ala Gly Val Val Ala Gly Leu Leu Glu Val Gly Trp Gln His Val Pro
180                 185                 190                 195 atc att gcc atg gag acc cat ggg gca cac tgc ttc aat gcg gcc atc      739
Ile Ile Ala Met Glu Thr His Gly Ala His Cys Phe Asn Ala Ala Ile
                200                 205                 210 aca gcc ggc aag ctg gtc aca ctt cca gac atc acc agt gtg gcc aag      787
Thr Ala Gly Lys Leu Val Thr Leu Pro Asp Ile Thr Ser Val Ala Lys
            215                 220                 225 agc ctg ggt gcc aag acg gtg gcc gct cgg gcc ctg gag tgc atg cag      835
Ser Leu Gly Ala Lys Thr Val Ala Ala Arg Ala Leu Glu Cys Met Gln
```

```
                  230                 235                 240
gtg tgc aag att cac tct gaa gtg gtg gag gac acc gag gct gtg agc     883
Val Cys Lys Ile His Ser Glu Val Val Glu Asp Thr Glu Ala Val Ser
    245                 250                 255 gct gtg cag cag ctc ctg gat gat gag cgt atg ctg gtg gag cct gcc     931
Ala Val Gln Gln Leu Leu Asp Asp Glu Arg Met Leu Val Glu Pro Ala
260                 265                 270                 275 tgt ggg gca gcc tta gca gcc atc tac tca ggc ctc ctg cgg agg ctc     979
Cys Gly Ala Ala Leu Ala Ala Ile Tyr Ser Gly Leu Leu Arg Arg Leu
                280                 285                 290 cag gcc gag ggc tgc ctg ccc cct tcc ctg act tca gtt gtg gta atc    1027
Gln Ala Glu Gly Cys Leu Pro Pro Ser Leu Thr Ser Val Val Val Ile
            295                 300                 305 gtg tgt gga ggc aac aac atc aac agc cga gag ctg cag gcc ttg aaa    1075
Val Cys Gly Gly Asn Asn Ile Asn Ser Arg Glu Leu Gln Ala Leu Lys
        310                 315                 320 acc cac ctg ggc cag gtc tga gggtcccat cctggcccca aagacccctg        1126
Thr His Leu Gly Gln Val  *
    325 agaggcccat ggacagtcct gtgtctggat gaggaggact cagtgctggc agatggcagt  1186 ggaagctgcc ctgtgcaact gtgctggctg cctcctgaag gaagccctcc tggactgctt  1246 cttttggctc tccgacaact ccggccaata aacactttct gaattgagtt tgcgaataaa  1306 aaaaaaaaaa aaaaaaaaaa a                                            1327

<210> SEQ ID NO 2
<211> LENGTH: 329
<212> TYPE: PRT
<213> ORGANISM: Homo sapien

<400> SEQUENCE: 2

Met Asp Gly Pro Val Ala Glu His Ala Lys Gln Glu Pro Phe His Val
1               5                   10                  15

Val Thr Pro Leu Leu Glu Ser Trp Ala Leu Ser Gln Val Ala Gly Met
            20                  25                  30

Pro Val Phe Leu Lys Cys Glu Asn Val Gln Pro Ser Gly Ser Phe Lys
        35                  40                  45

Ile Arg Gly Ile Gly His Phe Cys Gln Glu Met Ala Lys Lys Gly Cys
    50                  55                  60

Arg His Leu Val Cys Ser Ser Gly Gly Asn Ala Gly Ile Ala Ala Ala
65                  70                  75                  80

Tyr Ala Ala Arg Lys Leu Gly Ile Pro Ala Thr Ile Val Leu Pro Glu
                85                  90                  95

Ser Thr Ser Leu Gln Val Val Gln Arg Leu Gln Ala Glu Gly Ala Glu
            100                 105                 110

Val Gln Leu Thr Gly Lys Val Trp Asp Glu Ala Asn Leu Arg Ala Gln
        115                 120                 125

Glu Leu Ala Lys Arg Asp Gly Trp Glu Asn Val Pro Pro Phe Asp His
    130                 135                 140

Pro Leu Ile Trp Lys Gly His Ala Ser Leu Val Gln Glu Leu Lys Ala
145                 150                 155                 160

Val Leu Arg Thr Pro Pro Gly Ala Leu Val Leu Ala Val Gly Gly Gly
                165                 170                 175

Gly Leu Leu Ala Gly Val Val Ala Gly Leu Leu Glu Val Gly Trp Gln
            180                 185                 190

His Val Pro Ile Ile Ala Met Glu Thr His Gly Ala His Cys Phe Asn
```

```
            195                 200                 205
Ala Ala Ile Thr Ala Gly Lys Leu Val Thr Leu Pro Asp Ile Thr Ser
            210                 215                 220

Val Ala Lys Ser Leu Gly Ala Lys Thr Val Ala Arg Ala Leu Glu
225                 230                 235                 240

Cys Met Gln Val Cys Lys Ile His Ser Glu Val Val Glu Asp Thr Glu
                245                 250                 255

Ala Val Ser Ala Val Gln Gln Leu Leu Asp Asp Glu Arg Met Leu Val
            260                 265                 270

Glu Pro Ala Cys Gly Ala Ala Leu Ala Ala Ile Tyr Ser Gly Leu Leu
            275                 280                 285

Arg Arg Leu Gln Ala Glu Gly Cys Leu Pro Pro Ser Leu Thr Ser Val
        290                 295                 300

Val Val Ile Val Cys Gly Gly Asn Asn Ile Asn Ser Arg Glu Leu Gln
305                 310                 315                 320

Ala Leu Lys Thr His Leu Gly Gln Val
                325

<210> SEQ ID NO 3
<211> LENGTH: 990
<212> TYPE: DNA
<213> ORGANISM: Homo sapien
<220> FEATURE:
<221> NAME/KEY: CDS
<222> LOCATION: (1)...(990)

<400> SEQUENCE: 3 atg gac ggc cct gtg gca gag cat gcc aag cag gag ccc ttt cac gtg        48
Met Asp Gly Pro Val Ala Glu His Ala Lys Gln Glu Pro Phe His Val
1               5                   10                  15 gtc aca cct ctg ttg gag agc tgg gcg ctg tcc cag gtg gcg ggc atg        96
Val Thr Pro Leu Leu Glu Ser Trp Ala Leu Ser Gln Val Ala Gly Met
                20                  25                  30 cct gtc ttc ctc aag tgt gag aat gtg cag ccc agc ggc tcc ttc aag       144
Pro Val Phe Leu Lys Cys Glu Asn Val Gln Pro Ser Gly Ser Phe Lys
            35                  40                  45 att cgg ggc att ggg cat ttc tgc cag gag atg gcc aag aag gga tgc       192
Ile Arg Gly Ile Gly His Phe Cys Gln Glu Met Ala Lys Lys Gly Cys
        50                  55                  60 aga cac ctg gtg tgc tcc tca ggg ggt aat gcg ggc atc gct gct gcc       240
Arg His Leu Val Cys Ser Ser Gly Gly Asn Ala Gly Ile Ala Ala Ala
65                  70                  75                  80 tat gct gct agg aag ctg ggc att cct gcc acc atc gtg ctc ccc gag       288
Tyr Ala Ala Arg Lys Leu Gly Ile Pro Ala Thr Ile Val Leu Pro Glu
                85                  90                  95 agc acc tcc ctg cag gtg gtg cag agg ctg cag gcg gag ggg gcc gag       336
Ser Thr Ser Leu Gln Val Val Gln Arg Leu Gln Ala Glu Gly Ala Glu
            100                 105                 110 gtt cag ctg act gga aag gtc tgg gac gag gcc aat ctg agg gcg caa       384
Val Gln Leu Thr Gly Lys Val Trp Asp Glu Ala Asn Leu Arg Ala Gln
        115                 120                 125 gag ttg gcc aag agg gac ggc tgg gag aat gtc ccc ccg ttt gac cac       432
Glu Leu Ala Lys Arg Asp Gly Trp Glu Asn Val Pro Pro Phe Asp His
130                 135                 140 ccc cta ata tgg aaa ggc cac gcc agc ctg gtg cag gag ctg aaa gca       480
Pro Leu Ile Trp Lys Gly His Ala Ser Leu Val Gln Glu Leu Lys Ala
145                 150                 155                 160 gtg ctg agg acc cca cca ggt gcc ctg gtg ctg gca gtt ggg ggt ggg       528
Val Leu Arg Thr Pro Pro Gly Ala Leu Val Leu Ala Val Gly Gly Gly
```

-continued

```
              165                 170                 175
ggt ctc ctg gcc ggg gtg gtg gct ggc ctg ctg gag gtg ggc tgg cag      576
Gly Leu Leu Ala Gly Val Val Ala Gly Leu Leu Glu Val Gly Trp Gln
            180                 185                 190 cat gta ccc atc att gcc atg gag acc cat ggg gca cac tgc ttc aat      624
His Val Pro Ile Ile Ala Met Glu Thr His Gly Ala His Cys Phe Asn
            195                 200                 205 gcg gcc atc aca gcc ggc aag ctg gtc aca ctt cca gac atc acc agt      672
Ala Ala Ile Thr Ala Gly Lys Leu Val Thr Leu Pro Asp Ile Thr Ser
    210                 215                 220 gtg gcc aag agc ctg ggt gcc aag acg gtg gcc gct cgg gcc ctg gag      720
Val Ala Lys Ser Leu Gly Ala Lys Thr Val Ala Ala Arg Ala Leu Glu
225                 230                 235                 240 tgc atg cag gtg tgc aag att cac tct gaa gtg gtg gag gac acc gag      768
Cys Met Gln Val Cys Lys Ile His Ser Glu Val Val Glu Asp Thr Glu
                245                 250                 255 gct gtg agc gct gtg cag cag ctc ctg gat gat gag cgt atg ctg gtg      816
Ala Val Ser Ala Val Gln Gln Leu Leu Asp Asp Glu Arg Met Leu Val
            260                 265                 270 gag cct gcc tgt ggg gca gcc tta gca gcc atc tac tca ggc ctc ctg      864
Glu Pro Ala Cys Gly Ala Ala Leu Ala Ala Ile Tyr Ser Gly Leu Leu
        275                 280                 285 cgg agg ctc cag gcc gag ggc tgc ctg ccc cct tcc ctg act tca gtt      912
Arg Arg Leu Gln Ala Glu Gly Cys Leu Pro Pro Ser Leu Thr Ser Val
    290                 295                 300 gtg gta atc gtg tgt gga ggc aac aac atc aac agc cga gag ctg cag      960
Val Val Ile Val Cys Gly Gly Asn Asn Ile Asn Ser Arg Glu Leu Gln
305                 310                 315                 320 gcc ttg aaa acc cac ctg ggc cag gtc tga                              990
Ala Leu Lys Thr His Leu Gly Gln Val  *
                325
```